(12) United States Patent
Li (10) Patent No.: US 9,763,879 B2
(45) Date of Patent: *Sep. 19, 2017

(54) ORAL FILM CONTAINING OPIATE ENTERIC-RELEASE BEADS

(71) Applicant: LTS LOHMANN THERAPIE-SYSTEME AG, Andernach (DE)

(72) Inventor: Michael Li, Martinsville, NJ (US)

(73) Assignee: LTS Lohmann Therapie-Systeme AG, Andernach (DE)

(*) Notice: Subject to any disclaimer, the term of this patent is extended or adjusted under 35 U.S.C. 154(b) by 0 days.

This patent is subject to a terminal disclaimer.

(21) Appl. No.: 14/390,322

(22) PCT Filed: Apr. 11, 2013

(86) PCT No.: PCT/EP2013/057552
§ 371 (c)(1),
(2) Date: Oct. 2, 2014

(87) PCT Pub. No.: WO2013/153145
PCT Pub. Date: Oct. 17, 2013

(65) Prior Publication Data
US 2015/0064231 A1    Mar. 5, 2015

Related U.S. Application Data

(63) Continuation of application No. 13/445,716, filed on Apr. 12, 2012.

(51) Int. Cl.
*A61K 9/00* (2006.01)
*A61K 9/16* (2006.01)
(Continued)

(52) U.S. Cl.
CPC ............ *A61K 9/006* (2013.01); *A61K 9/0056* (2013.01); *A61K 31/485* (2013.01); *A61K 45/06* (2013.01);
(Continued)

(58) Field of Classification Search
None
See application file for complete search history.

(56) References Cited

U.S. PATENT DOCUMENTS

| 7,871,645 B2 | 1/2011 | Hall et al. |
| 2003/0082236 A1 | 5/2003 | Mathiowitz et al. |

(Continued)

FOREIGN PATENT DOCUMENTS

| CN | 101703777 A | 2/2001 |
| DE | 10 2006 027 796 A1 | 12/2007 |

(Continued)

OTHER PUBLICATIONS

Pharmaceutics, edited by Cui Fude, the fifth edition, People's Medical Publishing House, pp. 156-157.

*Primary Examiner* — Bethany Barham
*Assistant Examiner* — Barbara Frazier
(74) *Attorney, Agent, or Firm* — ProPat, L.L.C.

(57) ABSTRACT

A control release and abuse-resistant opiate drug delivery oral wafer or edible oral film dosage to treat pain and substance abuse is provided. The drug delivery oral wafer or edible oral film dosage includes a controlled release layer containing enteric-release beads dispersed in a polymer matrix. The enteric-release beads are formed from a therapeutic amount of an opioid agonist and/or pharmaceutically acceptable salt thereof and a sub-therapeutic amount of opioid antagonist and/or pharmaceutically acceptable salt thereof coated or encapsulated in an enteric-release polymer. The controlled release polymer matrix dissolves or disinte-
(Continued)

grates following administration or consumption of the oral wafer or edible oral film, releasing the enteric-release beads to be swallowed, with subsequent absorption of the active ingredients within the patient's intestines.

32 Claims, 1 Drawing Sheet (51) Int. Cl.
*A61K 31/485* (2006.01)
*A61K 45/06* (2006.01)
*A61K 47/32* (2006.01)
*A61K 47/38* (2006.01)

(52) U.S. Cl.
CPC .............. *A61K 47/32* (2013.01); *A61K 47/38* (2013.01); *A61K 9/1635* (2013.01); *A61K 9/1652* (2013.01)

(56) References Cited

U.S. PATENT DOCUMENTS

| 2006/0204559 | A1 | 9/2006 | Bess et al. |
| 2010/0285130 | A1* | 11/2010 | Sanghvi .................. A61K 9/006 424/484 |
| 2011/0033541 | A1 | 2/2011 | Myers et al. |

FOREIGN PATENT DOCUMENTS

| WO | WO 00/32255 A1 | 6/2000 |
| WO | WO 01/37808 A1 | 5/2001 |
| WO | WO 01/58447 A1 | 8/2001 |
| WO | WO 2007/144080 A2 | 12/2007 |
| WO | WO 2007/144081 A2 | 12/2007 |
| WO | WO 2007/144082 A2 | 12/2007 |
| WO | WO 2007/144083 A2 | 12/2007 |
| WO | WO 2007/144084 A2 | 12/2007 |
| WO | WO 2007/144085 A1 | 12/2007 |

* cited by examiner

ORAL FILM CONTAINING OPIATE ENTERIC-RELEASE BEADS

CROSS-REFERENCE TO RELATED APPLICATIONS

This application is being filed under 35 U.S.C. §371 as a National Stage Application of pending International Application No. PCT/EP2013/057522 filed Apr. 11, 2013, which claims priority to the following parent application: U.S. patent application Ser. No. 13/445,716, filed Apr. 12, 2012. Both International Application No. PCT/EP2013/057522 and U.S. patent application Ser. No. 13/445,716 are hereby incorporated by reference herein in their entirety.

FIELD OF THE INVENTION

The present invention relates to films providing controlled enteric release of therapeutic actives. The present invention more specifically relates to films providing a controlled enteric release of an opioid agonist, present in therapeutic amounts, and an opioid antagonist, present at a sub-therapeutic level.

BACKGROUND OF THE INVENTION

The search for a safe, orally ingested opiate analgesic is one of the oldest challenges known in medicinal chemistry. Opiates are incredibly well known for the treatment of acute or chronic severe pain, and are arguably one of the oldest drugs known to man. The market for chronic pain treatment is a substantial one, including the treatment of chronic pain associated with fibromyalgia, arthritis, sports injuries and malignancies. Current pain management protocols have resulted in a multi-billion dollar prescription market, with a pain management drug, hydrocodone/APAP, ranked number one in prescription drug sales in 2010.

Unfortunately, pain management drugs, particularly opiates, give rise to euphoria and other side effects when taken by healthy individuals, and thus opiates are extremely addictive. The diversion of prescription drugs for substance abuse is a societal issue that cannot be ignored.

Products are well known for treating narcotic addiction. Individuals addicted to narcotics may suffer from a serious dependence, resulting in potentially dangerous withdrawal. One well known method by which to treat narcotic addiction is to provide a reduced amount of opiate, in an amount sufficient to satisfy the addict's urge for the narcotic, but not in an amount sufficient to induce euphoria, commonly referred to as a "high." A product may include a particularly potent opiate, buprenorphine, along with an antagonist, naloxone, providing both a reduced euphoric effect and potentially avoiding opiate extraction (and subsequent abuse) by addicts. The narcotic antagonist binds to a receptor in the brain to block the receptor, thus reducing the effect of the opiate. Such a product was initially developed as a tablet. However, medicaments containing buprenorphine in tablet form have the potential for abuse. Films were subsequently developed that provide direct buccal absorption of the buprenorphine in a form that could not be easily removed from the mouth once administered, thereby retarding abuse. Such mucoadhesive film is described in United States Patent Application Publication No. 2011/0033541, hereby incorporated by reference herein.

There remains a need in the art for longer acting opiate drug forms for the treatment of addiction. There further exists a need in the art for opiates in film-form providing more extended treatment of chronic or acute pain.

SUMMARY Of ADVANTAGEOUS EMBODIMENTS OF THE INVENTION

The present invention thus provides a longer acting opiate drug forms for the treatment of addiction, acute pain, and chronic pain. The inventive oral films dosages include at least one layer formed from a controlled-release composition imparting intestinal release of a therapeutically effective amount of an opioid agonist or pharmaceutically acceptable salt thereof and a clinically effective amount of opioid antagonist or pharmaceutically acceptable salt thereof. The controlled-release composition includes at least one controlled-release matrix polymer and enteric-release beads dispersed within the matrix polymer. The enteric-release beads are formed from an enteric-release-bead composition including at least one enteric-release polymer and an opioid agonist and an opioid antagonist and/or their respective salts encapsulated therein. The control led-release composition further incorporates a pH adjuster in an amount effective to adjust the composition to a pH of about 2.0 to 3.0 pH units below the pKa of the opioid agonist, antagonist and their respective salts to bind the opioid to the enteric-release polymer. The oral film dosage or eon (rolled-release composition or layer further optionally includes one or more additives selected from taste masking agents, emulsifiers, plasticizers, colorants, antioxidants, microbial preservatives and permeation enhancers.

In particularly advantageous embodiments, the edible oral film dosages include buprenorphine as the opioid agonist along with naloxone as the opioid antagonist.

Further inventive aspects include methods by which to form the inventive oral film dosages, as well as their subsequent administration.

DETAILED DESCRIPTION OF ADVANTAGEOUS EMBODIMENTS OF THE INVENTION

The present invention generally related to the treatment of opioid dependence or chronic or acute pain in a patient using a dosage form that also hinders misuse of the narcotic. The present invention provides a method of treating chronic/acute pain or narcotic dependence by administering an orally dissolvable film dosage (also referred to herein as an oral wafer) providing a bioequivalent effect to the known opiate tablets and films, particularly SUBOXONE® tablets and films, but with enteric delivery of the active ingredients to provide a more prolonged efficacy. In particularly advantageous embodiments, the inventive film dosages preferably provides buccal adhesion to the user's mouth, rendering it difficult to remove after administration further hindering product misuse.

Figure 1:
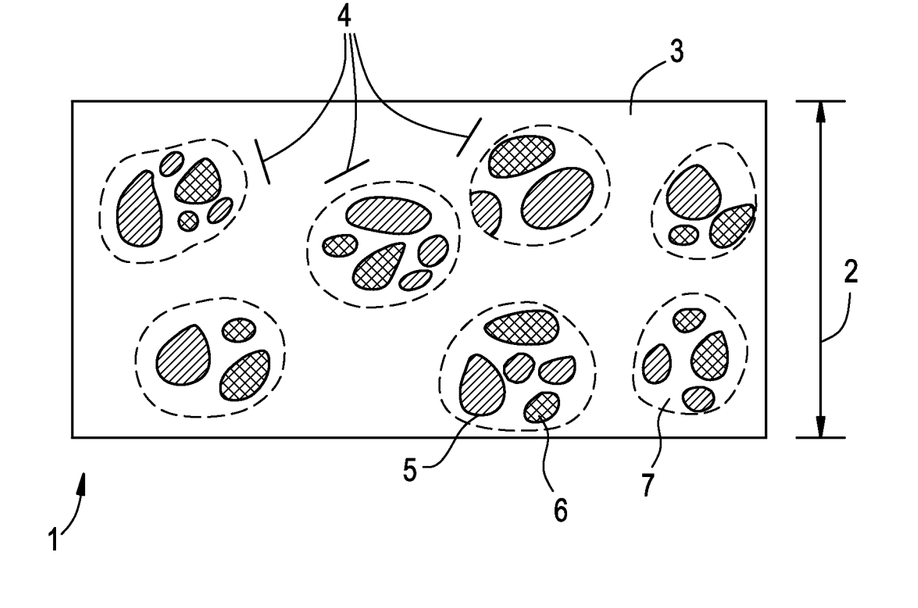
FIG. 1 is a cross-sectional view of an exemplary monolayer inventive oral film dosage.

An exemplary mono-layered inventive oral film dosage is illustrated in FIG. 1. The inventive oral film dosage (1) generally include at least one controlled-release layer (2) imparting enteric release of a clinically effective, i.e. therapeutic, amount of an opioid agonist and a clinically effective, i.e. subtherapeutic, amount of opioid antagonist. The composition used to form the controlled-release layer (i.e. the controlled-release composition) generally includes at least one controlled-release matrix polymer (3) and enteric-release beads (4) dispersed therein, with the enteric-release beads containing an opioid agonist (5) and an opioid antagonist (6) enveloped within an enteric-release polymer shell (7). Although not wishing to be bound by theory, Applicants hypothesize that the enteric-release polymer shell (7) is amorphous, hence there may be no visible, definite boundary between the polymer shell (7) and controlled-release matrix polymer (3), as illustrated within FIG. 1 by a dotted line. The controlled-release composition further comprises a pH adjuster in an amount effective to adjust the composition to a pH of about 2.0 to 3.0 pH units below the pKa of the opioid agonist, antagonist and/or their respective salts to bind the opioid agonist and antagonist and/or their respective salts to the polymer shell.

The oral film dosage is designed to disintegrate when applied to the oral cavity to release the opiate-containing enteric-release beads, which are then swallowed to be absorbed within the intestines. In particularly advantageous embodiments, the inventive oral film strip particularly disperses easily in the saliva of the oral cavity without the need for further oral liquids to release the enteric-release beads so that the active ingredients may be absorbed within the patient's intestines.

The saliva dispersible and disintegrable thin films used to form the inventive oral film strip matrices may be any known monographed film-forming material known in the art for use in flat-shaped or wafer-shaped administration forms for application to or in the oral region or on the mucous membranes of the mouth. The inventive oral film dosages generally comprise at (east one acetone-soluble, alcohol-soluble and/or water-soluble and/or water-dispersible film-forming polymer, particularly at least one saliva-soluble and/or saliva-dispersible film-forming polymer, that is capable of forming a suitably strong film upon casting in a pharmacologically acceptable solvent.

The controlled-release matrix polymer may thus be formed from any water, acetone and/or alcohol soluble or swellable pharmaceutical grade polymer that is either orally dissolvable/dispersible or orally consumable with gastric dissolution or swelling. The controlled release matrix polymer may also be formed from a combination of two or more such water, acetone and alcohol soluble or swellable polymers. The controlled-release matrix polymer provides cohesion to the dosage form during manufacture, storage and the like, but is sufficiently dissolved, swollen or disintegrated to release the enteric-release beads containing the opioid agonist and antagonist for enteric absorption subsequent to its administration.

Non-limiting exemplary polymers suitable for use as the controlled-release matrix polymer include one or more of cellulose and/or derivatives thereof; synthetic or natural gum, acrylic polymer and/or copolymer thereof, polyalkylene oxide, polyalkylene glycol, pullulan, polyvinyl pyrrolidone, polyvinyl alcohol, carrageanan, alginic acid and/or salts thereof, carboxyvinyl polymers, pectin and/or derivatives thereof, xanthan gum and/or derivatives thereof, and starch and/or derivatives thereof.

Exemplary cellulose derivatives suitable for use in forming the inventive oral film strips include methyl cellulose, ethyl cellulose, hydroxyethyl cellulose, hydroxypropyl methyl cellulose, carboxymethyl cellulose, sodium carboxymethyl cellulose, and mixtures thereof. In particularly advantageous embodiments, the inventive oral film strips are formed from a mixture of sodium carboxymethylcellulose or hydroxypropylmethyl cellulose and/or hydroxypropylcellulose. Sodium carboxymethylcellulose, commonly referred to as cellulose gum, is commercially available from any of a number of suppliers, including as AQUALON® CMC-7LF sodium carboxymethyl cellulose ("CMC") from Ashland Inc., of Covington, Ken. Hydroxypropylmethyl cellulose ("HPMC"), also referred to as hypromellose, is commercially available from a number of suppliers, including as METHOCEL® from Dow Chemical Company, Midland, Mich., BENECEL® from Ashland, Inc. of Covington, Ken. and PHARMACOAT® from Shin-Etsu Chemical Col, Ltd. of Tokyo, Japan and METOLOSE® also from Shin Etsu Chemical Co. Ltd of Tokyo. Hydroxypropylcellulose ("HPC") is commercially available as KLUCEL® from Hercules Incorporated, Wilmington, Del.

Advantageously, the inventive oral film dosages incorporate a film-forming mixture containing both lower and higher viscosity cellulose derivatives. The inventive oral film strips may incorporate a mixture of lower and higher viscosity HPMCs, for example. An exemplary range for the lower viscosity cellulose derivatives is from about 1.5 to 25 mPas, such as about 2 to 20 mPas, particularly about 3 mPas. An exemplary range for the higher viscosity cellulose derivative is from about greater than 25 to 100 mPas, such as from about 40 to 80 mPas, particularly about 50 mPas. HPMC having a viscosity of 3 mPas is commercially available as PHARMACOAT® 603 and HPMC having a viscosity of 50 is commercially available as METOLOSE® 60 SH50. The lower viscosity cellulose derivative is generally present within the film-forming mixture in a greater amount than the higher viscosity cellulose derivative. The lower viscosity cellulose derivative may be present within the film-forming mixture in any effective weight ratio in comparison to the higher viscosity cellulose derivative, such as a weight ratio ranging from about 1.5:1 to 6:1, particularly about 2.0:1 to 4:1, such as about 3:1 (lower viscosity cellulose derivative:higher viscosity cellulose derivative).

In particularly expedient embodiments, a mixture of sodium carboxymethylcellulose and hydroxypropylmethyl cellulose is used as the film-forming material or matrix, as this mixture has been determined to have both excellent film forming capabilities, oral film strip handling characteristics, beneficial mouth-feel as well as a fast dissolution time. The particular ratio of sodium carboxymethylcellulose to hydroxypropylmethyl cellulose is chosen to yield the desirable dissolution times and mouth-feel for a reasonably thin film and to further impart acceptable product handling characteristics. Although not wishing to be bound by theory, Applicants hypothesize that carboxymethyl cellulose imparts ease of dissolution in the mouth, and robust mouth-feel, while hydroxypropylmethyl cellulose imparts improved mechanical strength, particularly improved tear strength.

Exemplary synthetic or natural gums for use as the controlled-release matrix polymer include xanthan gum, tragacanth gum, guar gum, acacia gum, arabic gum, locust bean gum or mixtures thereof. Acceptable starches for use as the inventive controlled-release matrix polymer include bean starch, pea starch or mixtures thereof.

Exemplary acrylic polymer and/or copolymers that may be used as the controlled-release matrix polymer include methacrylic acid polymer, methacrylic acid copolymer, acrylic acid polymers, acrylic acid copolymers, polyacrylamide or mixtures thereof.

In especially advantageous embodiments, the controlled-release matrix polymer is a mucoadhesive polymer. Exemplary mucoadhesive polymers include one or more of edible silicone, polyacrylic acids, and cross-linked acrylic acid polymers, copolymers and interpolymers. Polymers of cross-linked acrylic acid are commercially available as CARBOPOL® polymer from Lubrizol Corp. of Wickliffe, Ohio.

The controlled-release matrix polymer is present within the controlled-release layer in an amount that typically ranges from about 30 to 70 wt %, such as from about 40 to 60 wt % and particularly from about 45 to 55 wt %, based upon the weight of controlled-release layer. For ease of discussion, the term "control led-release layer" as used herein refers to the controlled-release layer subsequent to drying, i.e. upon removal of a significant amount (if not all) of the solvent used in forming the controlled-release layer, unless indicated otherwise. In contrast, the term "controlled-release layer composition" refers to a mixture that includes the controlled-release matrix polymer, the enteric-release beads, optional additives and solvent, i.e. to the mixture prior to drying, unless indicated to the contrary.

The present dosage form is suitable for the extended release of any water-insoluble opioid agonist indicated to be acceptable within the U.S. Pharmacopeia/National Formulary. Non-limiting exemplary opioid agonists that may be included within the controlled-release composition include one or more of alfentanil, allylprodine, alphaprodine, amfepramone, amphetamine, amphetaminil, anileridine, apocodeine, apomorphine, asimadoline, axomadol, benzylmorphine, bezitramide, bremazocine, brifentanil, buprenorphine, butorphanol, carfentanil, clonitazene, codeine, cyclazocine, cyclorphan, cyprenorphine, cyprodime, deltorphin, desomorphine, dextromethorphan, dextromoramide, dextropropoxyphene, dezocine, diamorphine, diamorphone, diampromide, diacetylmorphine, dihydrocodeine, dihydrocodeinone, dihydroetorphine, dihydromorphine, dimenoxadol, dimephetamol, dimepheptanol, dimethylthiambutene, dioxyaphetyl butyrate, diphenoxylate, dipipanone, diprenorphine, dronabinol, Met-enkephalin, Leu-enkephalin, dynorphin A, dynorphin B, β-endorphin, eptazocine, endorphin, ethoheptazine, 14-ethoxymetopon, ethylketocyclazocine, ethylmethylthiambutene, ethylmorphine, etonitazene, etorphine, extromoramide, fencamfamine, fenethylline, fenproporex, fentanyl, a-methylfentanyl, beta-funaltrexamine, β-hydroxy-3-methylfentanyl, heroin, hydrocodone, hydromorphone, hydromorphodone, hydroxymethylmorphinan, hydroxypethidine, isomethadone, ketobemidone, kyotorphin, levo-α-acetylmethadol, levacetylmethadol, levallorphan, levomethadone, levomethadyl acetate, levallorphan, levorphanol, levophenacylmorphan, lofentanil, Lofexidine, loperamide, malbuphine, mazindol, mefenorex, meperidine, meprobamate, meptazinol, metazocine, methadone, metopon, methyldihydromorphine, methyldihydromorphinone, methylmorphine, methylnaltrexone, methylphenidate, methyprylon, metopon, mirfentanil, modafmil, morphiceptin, morphinan, morphine, myrophine, nabilone, nalbuphene, nalbuphine, nalmefene, nalorphine, naloxone, naloxone benzoylhydrazon, naltrexone, naltriben, naltrindole, naltrindole isothiocyanate, narceine, natbuphine, nicomorphine, nor-binaltorphimine, norlevorphanol, normethadone, nalorphine, normorphine, norpipanone, noscapine, ohmefentanyl, o-methylnaltrexone, opium, onitazene, oxycodone, oxymorphone, papaveretum, papaverine, paregoric, pemoline, pemoline, pentazocine, pethidine, phendimetrazine, phendimetrazone, phenmetrazine, phenadoxone, phenomorphan, phenazocine, phenoperidine, pholcodeine, piminodine, pipradrol, piritramide, premorphine, profadol, properidine, propheptazine, promedol, properidine, propiram, propoxyphene, propylhexedrine, remifentanil, spiradoline, sufentanil, sufentanyl, tapentadol, thebaine, tramadol, trefentanil, tilidine, viminol or their salts, or opioids of the phenanthrene, morphinan, benzomorphan, methadone, phenylpiperidine, propionanilide 4-anilidopiperidine, 4-aryl piperidines, and 4-heteroarylpiperidines class. The opioid agonist may be present in the form of its tree base, or in the form of a salt, prodrug, ester, analog, derivative, solvate, complex, polymorph, hydrate, racemate or as an individual diastereoisomers and/or their enantiomeric isomers and their respective glucuronide derivative. In particularly advantageous embodiments, the opioid agonist is buprenorphine and/or a pharmaceutically acceptable salt thereof. For ease of discussion, the term "agonist" as used herein includes both the agonist and/or its pharmaceutically acceptable salts unless stated to the contrary.

Furthermore, as used herein the term "water-insoluble" (or other-polar-solvent-insoluble) refers to materials or ingredients, e.g. agonists, antagonists, enteric polymers and the like, that have a solubility in water (or other specific polar-solvent) of less than 10 mg/ml, such as a solubility in water (or other specific polar-solvent) of less than 1 mg/ml, and particularly a solubility in water (or other specific polar solvent) of less than or equal to 100 µg/ml.

The opioid agonist is present within the controlled release composition in a therapeutically effective amount. Exemplary opioid agonist therapeutically effective amounts for inventive dosages intended for the treatment of opiate addiction include greater than 2 milligrams; such as from about 2 mg to about 16 mg per dosage, particularly from about 4 mg to about 12 mg per dosage. Exemplary opioid agonist therapeutically effective amounts for dosages intended to control acute pain in non-opioid tolerant individuals range from about 100 to 400 micrograms, such as approximately 200 micrograms. Exemplary opioid agonist therapeutically effective amounts for dosages intended to control chronic pain ranges from about 20 to 70 micrograms per hour per dosage.

The present dosage form is likewise suitable for the extended release of any water-insoluble opioid antagonist indicated to be acceptable within the U.S. Pharmacopeia/National Formulary for use in conjunction with opioid agonists. Non-limiting exemplary opioid antagonists that may be included within the controlled-release composition include one or more of alazocine, amiphenazole, butorphanol, chlornaltrexamine, cyclocinnamox, cyclazacine, cyclazocine, cyclorphan, cyprenorphine, diprenorphine, etazocine, β-funaltrexamine, levallorphan, meptazinol, metazocine, nadide, nalbuphine, nalide, nalmefene, nalmefendiprenorphine, nalmexone, nalorphine, nalorphine dinicotinate, naloxone, 6-amino-naloxone, N-methylnaloxone, nor-binaltorphimine, naltrendol, naltrexone, 6-amino-naltrexone, 7-benzylidenenaltrexone, N-methymaltrexone, naltrindole, naluphine, oxilorphan, pentazocine, piperidine-N-alkylcarboxylate opioid antagonists, and opioid antagonist polypeptides.

The opioid antagonist may be present in the form of its free base, or in the form of a salt, prodrug, ester, analog, derivative, solvate, complex, polymorph, hydrate, racemate or as an individual diastereoisomers and/or their enantiomeric isomers and their respective glucuronide derivative. In particularly advantageous embodiments, the opioid antagonist is naloxone and/or a pharmaceutically acceptable salt thereof. For ease of discussion, the term "antagonist" as used herein includes both the agonist and/or its pharmaceutically acceptable salts unless stated to the contrary.

The opioid antagonist is generally present within the controlled release composition in a clinically effective amount. The term "clinically effective amount of opioid antagonist" refers to a subtherapeutic amount of opioid antagonist when administered orally, i.e. the opioid antagonist will elicit no significant therapeutic effect via the oral route. The term "clinically effective amount of opioid antagonist" more specifically means the minimum amount of opioid antagonist possible or conventionally used to effectively deter misuse of the inventive film dosages, e.g. by active ingredient extraction and subsequent intravenous injection. Hence the term "clinically effective amount of opioid antagonist" as used herein refers to an orally ineffective dose but intravenously effective dose of opioid antagonist sufficient to deter abuse of the inventive film dosages.

The opioid antagonist is generally present in significantly lower amounts than the opioid agonist. Conventional dosages may include the opioid antagonist in a weight ratio of about 6:1 to 2:1 agonist to antagonist, such as a weight ratio of about 4:1 (agonist:antagonist).

Exemplary opioid antagonist, clinically effective amounts within the inventive dosages intended to treat opiate addiction may include greater than 0.5 milligrams antagonist per dosage, such as from about 0.5 to about 4 mg per dosage; particularly from about 1 mg to about 3 mg per dosage. Exemplary opioid antagonist clinically effective amounts for dosages intended to control acute pain in non-opioid tolerant individuals ranges from about 25 to 100 micrograms per dosage, such as approximately 50 micrograms per dosage. Exemplary opioid antagonist, clinically effective amounts for dosages intended to control chronic pain ranges from about 5 to 17.5 micrograms per hour per dosage, in further alternative embodiments, such as inventive dosages administered solely within a medical facility, the inventive dosages may contain no opioid antagonist.

The inventive oral film dosages advantageously provide a bioequivalent result, e.g. a bioequivalent release, to commercially available SUBOXONE® products, particularly for advantageous embodiments in which the agonist is buprenorphine and the antagonist is naloxone. The inventive oral film dosages thus advantageously exhibit an AUC value so as to provide a bioequivalent result to a commercially available SUBOXONE® tablet. In that regard, the oral film dosage composition may be prepared to provide a Cmax and/or AUCinf value for each of the agonist and antagonist that provides a bioequivalent release to a commercially available SUBOXONE® tablet i.e. providing 80% to 125% of the Cmax and AUC values for a given active within a commercial product. For example, the oral film dosages may be tailored in advantageous embodiments to provide an in vivo plasma profile having an agonist Cmax ranging from 0.624 to 0.975 ng/ml, such, as an agonist Cmax of about 6.4 ng/ml, and an agonist AUC value of 5.431 to 8.486 hr*ng/ml, with a corresponding antagonist Cmax of less than about 400 pg/ml and antagonist AUCinf value of less than about 1030 hr*pg/ml.

The opioid agonist and opioid antagonist (which may also be referred to cumulatively hereinafter as "active ingredients") are present within enteric release beads suspended in the controlled-release matrix polymer. The enteric-release beads are formed by coating, suspending and/or dissolving the active ingredients within at least one enteric-release polymer that protects the active ingredients until they are released from the enteric-release polymer within the intestine. As will be discussed in greater detail below, the active ingredients are initially dissolved within a solvent to which the enteric-release polymer, and optional auxiliaries, are added, and the enteric-release beads subsequently harvested. For ease of discussion, the term "enteric-release-bead" as used herein refers to the enteric-release beads subsequent to harvest, i.e. upon removal of a significant amount (if not all) of the enteric-release-bead-solvent, unless indicated otherwise. In contrast, the term "enteric-release-bead composition" refers to a mixture that includes the enteric-release polymer, agonist, antagonist, optional auxiliaries, and solvent, i.e. the mixture prior to bead harvest, unless indicated to the contrary. Furthermore, for ease of discussion, the term "coats" and "encapsulates" should be construed as equivalent terms unless indicated to the contrary.

Advantageously, the same enteric-release polymer or enteric-release polymer blend is used to coat both the opioid agonist and opioid antagonist. In alternative embodiments, the opioid agonist and opioid antagonist may be coated with different enteric-release polymers or polymer blends.

The harvested enteric-release beads generally have a core/shell or core/islands configuration, with the enteric-release polymer forming the shell or coating around one or more cores or islands formed from the opioid agonist and/or opioid antagonist. The shell typically envelopes or encases the active ingredients, such that at least 50% of the active ingredients surface area is covered by or disposed within the shell formed by the enteric-release polymer. In advantageous embodiments, at least 75% of the active ingredients surface area, and particularly 100% of the active ingredient surface area is covered by or disposed within the shell or coating formed by the enteric-release polymer. A given enteric-release bead may contain either opioid agonist, opioid antagonist or, in advantageous embodiments, a mixture of opioid agonist and opioid antagonist.

Polymer suitable for use as the enteric-release polymer that coats the active ingredients include any water-insoluble polymer indicated to as acceptable within the U.S. Pharmacopeia/National Formulary as a coating for the gastric and/or enteric delivery of active ingredients. At least a portion of the enteric polymers are formed from cellulose, vinyl or acrylic derivatives that are insoluble or only moderately soluble at the lower pH found in gastric fluids but are readily soluble, swellable or permeable at the higher pH found in intestinal fluids, thereby allowing the majority (i.e. at least 50%) of the active ingredient to diffuse out into the intestinal fluid. Applicants have found that by selecting an enteric-release polymer or polymer blend components with specific dissolution properties at predetermined pHs, the enteric-release polymer coating allows the vast majority, if not the entirety, of the coated active ingredients to pass through the stomach for subsequent release within the intestines as the coating becomes more solubilized and/or permeable. As used herein, the term enteric-release polymer(s) include polymers soluble in fluids below a pH of about 5, e.g. polymers soluble at the pH of stomach fluids, solely for ease of discussion, as these polymers are generally used as a component within an overall enteric-release polymer blend intended to release at least the majority of the active ingredients within the intestines.

In particularly advantageous embodiments, the enteric-release polymer is a blend or mixture, such as a blend or mixture containing one or more enteric-release polymers soluble at a lower pH and one or more enteric-release polymers soluble at a higher pH. The enteric-release polymer(s) soluble at a lower pH may be soluble in fluids below a pH of about 5, such as a pH of less than about 4.5, particularly a pH ranging from about 1 to 2 (e.g. the pH of stomach fluids). The enteric-release polymers) soluble at higher pHs may be soluble in fluids having pH of greater than about 5.5, such as a pH of greater than about 6.0, and particularly a pH of greater than about 7.0 up to about 8.5, (e.g. the pH of intestinal fluids). In such advantageous embodiments, the enteric-release polymer(s) soluble at a lower pH dissolve within the stomach fluid, thereby protecting the active ingredients during manufacture and ingestion yet allowing the thinner enteric-release polymer coating that remains, i.e. the enteric-release polymers) soluble at a higher pH, to more easily release the majority (if not all) of the active ingredients within the intestines. Exemplary weight ratios of blends containing enteric-release polymer(s) soluble at a lower pH and enteric-release polymers) soluble at a higher pH typically range from 1:10 to 10:1 (weight of enteric-release polymer(s) soluble at lower pH:weight of enteric-release polymer(s) soluble at a higher pH), such as about 1:5 to 5:3, and particularly 1:1.

Exemplary enteric-release polymers suitable for use in coating/encapsulating the active ingredients include one or more of hydroxypropyl methyl cellulose acetate succinate, hydroxypropyl methyl cellulose phthalate, cellulose acetate phthalate, polyvinyl acetate phthalate, and polymethacrylate copolymer. In particularly advantageous embodiments the enteric-release polymer is polymethacrylate copolymer, specifically a polymethacrylate copolymer blend or mixture including (i) cationic polymethacrylate copolymer derived from dimethylaminoethl methacrylate and other neutral methacrylic acid esters and (ii) anionic polymethacrylate copolymer derived from methacrylic acid and acrylate. In such advantageous embodiments, the cationic polymethacrylate copolymer may dissolve partially or fully within the stomach (e.g. in a pH of below about 5), with the remaining anionic polymethacrylate copolymer subsequently dissolving within the intestines (e.g. in a pH of greater than about 7.0).

Exemplary cationic polymethacrylate copolymers include poly(butyl methacrylate, (2-dimethyl aminoethyl) methacrylate, methyl methacrylate copolymer. Poly(butyl methacrylate, (2-dimethyl aminoethyl) methacrylate, methyl methacrylate copolymer having a ratio of respective monomers of 1:2:1 is commercially as EUDRAGIT® E from Evonik Rohm GmbH of Darmstadt, Germany.

Exemplary anionic polymethacrylate copolymers include copolymers derived from methacrylic acid and either methyl methacrylate or ethyl acrylate. In especially expedient embodiments, the anionic polymethacrylate copolymers derived from methacrylic acid and either methyl methacrylate or ethyl acrylate have a ratio of methacrylic acid to methyl methacrylate or ethyl acrylate monomer of either 1:1 or 1:2. Anionic polymethacrylate copolymer having a methacrylic acid to methyl methacrylate or ethyl acrylate monomer ratio of 1:1 are commercially available as EUDRAGIT® L from Evonik Rohm GmbH of Darmstadt, Germany. Anionic polymethacrylate copolymer having a methacrylic acid to methyl methacrylate monomer ratio of 1:2 are commercially available as EUDRAGIT® S from Evonik Rohm GmbH of Darmstadt, Germany.

The enteric-release polymer is typically present within the enteric-release-beads in amounts ranging from about 5 to 60 wt %, such as from about 10 to 40 wt %, particularly from about 15 to 30 wt %, based on the weight of the enteric-release-beads. In advantageous embodiments in which the enteric-release polymer Ls a blend of cationic polymethacrylate copolymer and anionic methacrylate copolymer, the cationic copolymer and anionic copolymer are generally present in a ratio ranging from about 10:1 to 1:10, such as a 1:1 weight ratio of cationic polymer to anionic polymer.

The opioid agonist and/or salt thereof is generally present within the enteric-release-beads in amounts ranging from about 10 to 90 wt %, such as from about 20 to 80 wt %, particularly from about 30 to 70 wt %, based on the weight of the enteric-release-beads.

The opioid antagonist and/or salt thereof is generally present within the enteric-release-bead composition in far lower amounts than the opioid agonist, such as amounts ranging from about 1 to 30 wt %, such as from about 5 to 25 wt %, particularly from about 10 to 20 wt %, based on the weight of the enteric-release-beads.

The enteric-release polymer or enteric-release-bead composition may further optionally include any conventional additives or auxiliaries known to those skilled in the art.

The enteric-release polymer or enteric-release-bead-shell composition may further include one or more of at least one bead stabilizer, plasticizer or emulsifier.

Exemplary bead stabilizers include any compound or polymer that decreases or eliminates clumping and/or aggregation of the enteric-release beads as they are being formed and/or harvested. Suitable bead stabilizers include cellulose and/or cellulosic derivatives, such as hydroxy-propyl, methyl cellulose, methyl cellulose, and the like, present in an amount to substantially or fully eliminate enteric-release bead clumping. METOLOSE® 60 SH 50 from Shin Etsu Chemical Co. Ltd of Tokyo, particularly well suited for use as the bead stabilizer, has a methoxy content ranging from about 28.0 to 30.0% and a hydroxypropoxy content ranging from 7.0 to 12.0%. Typical bead stabilizer amounts range from about 1 to 10 wt %, such as from 3 to 7 wt %, particularly about 4 wt %, based on the weight of the enteric-release beads.

Exemplary plasticizers include one or more of alkylene glycols, polyalkylene glycols, glycerol, triacetin, deacetylated monoglyceride, polyethylene glycols, diethyl salate, and triethyl citrate.

Exemplary emulsifiers include one or more of sodium lauryl sulfate and polysorbate 80. The conventional additives or auxiliaries may be present within the enteric-release-beads in conventional amounts known to those skilled in the art, such as amounts ranging from about 1 to 10 wt %, based upon the weight of the enteric-release beads.

The enteric-release beads are present within the controlled-release layer in an amount that typically ranges from about 5 to 50 wt %, such as from about 10 to 45 wt %, particularly from about 20 to 40 wt %, based upon the weight of controlled-release layer.

The enteric-release beads may further advantageously have a target bead size of up to 2.5 mm (i.e. average diameter) with no more than 10 percent variation over this size, to a maximum size of 2.8 mm, in conformance with FDA general recommendations for size of beads in drug products. In that regard, the FDA has indicated that beads having the foregoing size allow for patient swallowing without stimulating the urge to chew. In particularly advantageous embodiments, the enteric-release beads range are quite small, ranging in size from about 5 to 400 microns, such as from about 10 to 200 microns, in diameter or width. The enteric beads are not limited in their geometry, and may be generally spherical, rounded amorphous, polygonal or any other shape.

The enteric beads release the majority, if not all, of the active ingredients within the intestinal fluids. In that regard, the enteric release beads release at least 50 wt %, such as at least 75 wt % and preferably 100 wt % of the active ingredient within about 5 minutes in an aqueous solution at a pH of 7.4, i.e. a pH reflecting conditions found in intestinal fluid. The enteric release beads release significantly less active ingredients within lower pHs, such as less than 50 wt %, preferably less than 25 wt % and particularly preferably less than about 20 wt % within about 5 minutes in an aqueous solution at a pH of 4.5. Advantageously, the enteric release beads release minimal or no active ingredients within the extremely low pHs found in the stomach, i.e. pHs ranging from about 1 to 2, such as a release of less than 5 wt %, preferably less than 2 wt % and more preferably less than about 1 wt % within about 5 minutes in an aqueous solution at a pH of 2. In alternative, less preferred embodiments, it is also envisioned that "enteric-release" formulations could be formed to provide a release of the majority, if not all, of the active ingredients within the stomach, should a need for such embodiment ever arise.

The controlled release layer also includes at least one pH adjuster to lower the pH of the controlled release composition to between about 2.0 to 3.0 units below the pKa of the opioid agonists and opioid antagonists to effect binding of the opioid agonists and opioid antagonists to the enteric-release polymer. The amount of pH adjuster suitable for incorporation into the controlled release composition may be readily determined by one skilled in the art, for example using the Henderson Hasselbalch equation. The pKa for buprenorphine, an exemplary opioid agonist, is understood to be about 8.31. The pKa for naloxone, an exemplary opioid antagonist, is said to be about 7.94. Accordingly, the pH adjuster is generally present in an amount effective to impart a pH ranging from about 4.94 to 6.31, such as a pH of from about 5.0 to 6.0, to the controlled release composition and/or controlled release layer. Typically, the pH adjuster is present in an amount ranging from about 3.0 to 10.0 wt %, such as from 4 to 9 wt %, particularly front about 4.5 to 8 wt %, based upon the weight of the controlled release layer. Exemplary pH adjusters include any monographed pH adjuster suitable for use in pharmaceuticals, such as one or more of sodium citrate, citric acid, tartaric acid, sodium tartrate, acetic acid, sodium acetate and the like.

In advantageous embodiments, the inventive film dosages, particularly the controlled release layer (and the composition used to form it) further includes optional additives selected from one or more taste masking ingredients, emulsifiers, plasticizers, colorants, antioxidants, microbial preservatives, permeation enhancers.

In especially beneficial embodiments, the taste masking ingredients completely block any residual unpleasant taste associated with the active ingredients. Exemplary taste masking ingredients include one or more of sweetener(s), flavouring agents, cooling sensation agent(s), and taste receptor blockers). In especially expedient embodiments, multiple components are contained within the secondary taste masking composition or blend.

Exemplary sweeteners include any monographed sweetener, including dextrose, lactose, fructose, mannitol, sucrose, trehalose, sucralose, xylitol, mannitol, aspartame, saccharin, sorbitol, sodium saccharin, sodium cyclamate, acesulfame, honey, isomalt, maltodextrin, dextrin, dextrates and mixtures thereof. The sweeteners may be included in the controlled release layer in any effective amount, such as from about 0 to 3 wt %, such as from about 0.5 to 1.5 wt %, based upon the weight of the controlled release layer.

Exemplary flavouring agents include any flavouring agent indicated to be acceptable within the U.S. Pharmacopeia/National Formulary, including various essential oils or extracts of menthol, wintergreen, peppermint, sweet mint, spearmint, vanillin, cherry, butterscotch, chocolate, cinnamon, clove, lemon, orange, raspberry, rose, spice, violet, herbal, fruit, strawberry, grape, pineapple, vanilla, peppermint, peach, kiwi, papaya, mango, coconut, tutti fruitti, apple, coffee, plum, watermelon, nuts, green tea, grapefruit, banana, butter, chamomile, masking flavour, and mixtures thereof. In especially beneficial embodiments the controlled release layer incorporates one or more flavouring agents selected front lime, tutti frutti, cherry, wintergreen, spearmint, peppermint, and orange. Suitable pharmaceutical grade flavouring agents may by acquired from any of a number of suppliers. In addition to their use as flavorants, several of the foregoing flavouring agents may serve as cooling agents, as well.

The flavouring agents may be included within the controlled release layer in any effective amount, such as from about 1.0 to 5.0 weight %, such as from about 2.0 to 3.0 wt %, based upon the weight of the controlled release layer.

A masking flavour may also be incorporated within controlled release layer, particularly in combination with further flavouring agents. Masking flavours are commercially available from a number of suppliers, including Firmenich of Geneva, Switzerland. The masking flavouring may be included in any effective amount, such as from about 0 to about 2.5 wt %, based upon the weight of the controlled release layer.

One or more cooling sensation agents may also be included within controlled release layer to diminish or altogether eliminate any burning sensation, particularly any residual burning sensation, associated with the active ingredients. Exemplary cooling sensation agents include essential oils or extracts of menthol, wintergreen, peppermint, sweet mint, spearmint, and mixtures thereof. The cooling sensation agent may be included in any effective amount, such as from about 0 to about 5.0 weight %, such as from about 1.0 to 3.0 weight %, based upon the weight of the controlled release layer.

One or more taste receptor blockers may also advantageously be included within the controlled release layer. Exemplary taste receptor blockers include any monographed taste receptor blocker. In expedient embodiments, the inventive oral film strips include PEG-40 hydrogenated castor oil as taste receptor blocker. PEG-40 Hyrdrogenated Castor Oil is commercially available as CREMOPHOR® from BASF SE of Ludwigshafen, Germany.

The taste receptor blockers may be included within the controlled release layer in any effective amount, such as from about 0.0 to about 6.5 weight %, and particularly from about 0.30 to 4.50 wt %, based upon the weight of the controlled release layer.

The controlled release layer can additionally beneficially include at least one emulsifier. Any well-known water-soluble monographed emulsifier is suitable for use in the inventive oral film strips. Examples of suitable emulsifying agents include, but are not limited to, castor oil derivatives, cetyl and palmityl alcohol, ethanol, hydrogenated vegetable oils, polyvinyl alcohol, simethicone, sorbitan ester, glyceryl monostearate, polyoxyethylene alkyl ethers, polyoxyethylene stearates, poloxamer, polyethylene sorbitan fatty acid esters and mixtures thereof.

The emulsifier may be included within the controlled release layer in any amount effective, such as in amounts ranging from about 0 to 2.25 wt %, particularly from 0.50 to 1.50 wt %, based on the weight of the controlled release layer.

Additional ancillary components suitable for incorporation within the inventive oral film dosages, particularly the controlled release layer include, but are not limited to one or more of the following pharmaceutically-acceptable excipients: bioadhesives for mucosal binding (also referred to as mucoadhesives), coloring agents, stabilizing agents, antioxidants, fillers, permeation enhancers, plasticizers and microbial preservatives. Such ancillary components are included within the inventive oral film strips in amounts considered conventional by one skilled in the art for the given component.

Mucoadhesive(s) adhere to the oral mucosal membranes, such as the surfaces of cheek, palate or tongue, as known in the art. Exemplary mucoadhesives include edible silicone and polyacrylic acids, particularly polymers of acrylic acid cross-linked with polyalkenyl ethers or divinyl glycol such as the family of CARBOPOL® polymers, copolymers and interpolymer, commercially available from Lubrizol Corporation of Wickliffe, Ohio.

The examples of suitable colorants include approved edible pigments, dyes, natural food colors, and synthetic colorants such as FD&C coloring agents and mixtures thereof.

The examples of suitable stabilizers and/or antioxidants include chelating agents, such as ethylenediaminetetraacetic acid ("EDTA"), ethylene glycol tetraacetic acid ("EGTA"), sodium bisulfite, sodium metabisulfite, ascorbic acid, ascorbyl palmitate and mixtures thereof.

Exemplary fillers include any water soluble inert filler. Suitable water soluble inert fillers for incorporation in the inventive oral film dosages include mannitol, xylitol, glucose, fructose, sucrose, sucralose, lactose, trehalose, maltodextrin, dextran, dextrin, modified starches, dextrose, sorbitol, dextrates and mixtures thereof.

The inventive film dosage, particularly the controlled release layer, may also contain natural or synthetic permeation enhancers. As well understood in the art, a "permeation enhancer" is a natural or synthetic compound which facilitates the absorption of an active agent through a mucosal surface, such as the surface of the intestines. Exemplary permeation enhancers include anionic surfactants, such as sodium lauryl sulfate and sodium laurate; cationic surfactants, such as cetylpyridium chloride; non-ionic surfactants, such as poloxamer, Brij, Span, Myrj, and Tween; bile salts; sodium glycodeoxycholate; sodium glycocholate, sodium taurodeoxycholate, sodium taurocholate, Azone®; fatty acids, such as oleic and caprylic acid; cyclodextrins, such as α-, β-, γ-cyclodextrin, methylated β-cylcodextrins; chelators, such as EDTA, sodium citrate and poly acrylates; polymers, such as chitosan, trimethyl chitosan and cationic amino acids, such as poly-L-arginine and L-lysine. Brij is the tradename for a family of nonionic polyoxyethylene commercially available from a number of suppliers. Span is the tradename for a family of sorbitan surfactants, such as sorbitan trioleate (Span 85) and sorbitan tristearate (Span 65) and the like, commercially available from a number of suppliers. Myrj is a tradename for a family of polyethoxylated fatty acid commercially available from a number of suppliers, such as polyoxyethylene monostearate (Myrj 49) and the like. Tween is the tradename for a family of polyoxyethylene sorbitan or polysorbate surfactants, such as polyoxyethylene sorbitan trioleate (Tween 85) and polysorbate 80 (Tween 80) commercially available from a number of suppliers. Azone is a tradename for 1-Dodecylhexahydro-2h-Azepin-2-One.

Suitable plasticizers for incorporation into the inventive film dosage, particularly the controlled release layer include any monographed plasticizer. Exemplary plasticizers include, but not limited to, alkylene glycols, polyalkylene glycols, glycerol, triacetin, deacetylated monoglyceride, polyethylene glycols, diethyl salate, triethyl citrate, and mixtures thereof.

The inventive film dosage particularly the controlled release layer, may also contain microbial preservatives, such as butylated hydroxyanisol, butylated hydroxyltoluene, parabens, parabens derivatives, sorbic acids and derivatives, benzoic acid and derivatives, propionic acid and derivatives, acetic acid and derivatives and mixtures thereof.

The inventive oral film dosages may be in the form of either a single or multiple layered film. For multi-layered embodiments, each or the individual layers may contain either identical or different excipients in either the same or differing amounts. Various film layers may be formulated to exhibit differing dissolution times or contain various active ingredient loadings, for example. In particularly advantageous embodiments, the inventive films include a non-mucoadhesive controlled release layer in combination with a layer formed from muco-adhesive polymer.

The inventive oral film dosages are prepared in thicknesses conventional with wafer or thin film-based oral pharmaceutical films, such as thicknesses ranging from 50 to 120 microns, particularly about 60 to 115 microns.

The inventive oral film dosages may have any shape known in the art for pharmaceutical oral film strips or dosages. For example, the oral film dosages may have a a round, oval, square, rectangular or other irregular geometric shape. The inventive oral film dosages may further have any dimensions known in the art as suitable for oral film strips, oral wafers or oral film dosages.

Suitable solvents suitable for use in forming the enteric-release beads, controlled release layer and/or oral film dosage include one or more of purified water, acetone, ethanol or other pharmacologically acceptable alcohol that is 4 carbons or less in length. The pharmacologically acceptable solvents may be used in any combination and any solvent ratio, unless indicated to the contrary.

For example, particular solvents are initially used to form the enteric-release beads, especially less polar solvents (also referred to herein as non-polar solvents) are used in amounts effective to suspend the enteric-release polymer and active ingredients. Additional solvent having a greater polarity (also referred to herein as polar solvent), such as water, is then used in an amount effective to initially nucleate and subsequently harden the resulting enteric-release beads within the polymer solution. For ease of discussion, as used herein, the term "polar" solvent and "non-polar" solvent are merely used as relative terms indicating the polarity of a given solvent in comparison to water (as the most polar solvent). Although not wishing to be bound by theory, Applicants generally hypothesize that solvents having a comparatively lower Hansen solubility parameter value for polar bonds, i.e. $\delta P$, of less than about 13 should be considered non-polar solvents, and solvents having a more elevated Hansen solubility parameter value for polar bonds, such as a $\delta P$ of greater than about 13, should be considered polar solvents. Exemplary solvents having a $\delta P$, of less than 13 include acetone ($\delta P=10.4$); ethanol ($\delta P=8.8$); n-propanol ($\delta P=6.8$); isopropanol ($\delta P=6.1$); n-butanol ($\delta P=5.7$) and methanol ($\delta P=12.3$). Exemplary solvents having a $\delta P$ of greater than 13 include water ($\delta P=16.0$ $\delta P$).

Solvents are also used in amounts effective to dissolve and/or suspend the entirety of the ingredients within the controlled release layer into a liquid mass prior to oral film dosage formation, particularly oral film dosage casting, coating or extrusion. The resulting liquid mass has a moderately elevated viscosity, as is conventional for film-forming blends used to form edible oral film strips or wafer thin film dosages. The solvent may be present in amounts of up to 95% within the liquid mass, such as an amount ranging from about 60 to 90%, based on the weight of the casting/coating/extrusion composition. The solvent is then removed after casting, coating or extruding the wet film in a subsequent drying step during oral film dosage production.

The present invention further provides methods for preparing the edible oral film dosages.

The inventive methods generally include forming enteric-release beads containing the active ingredients and incorporating the same into a pH adjusted solution containing the controlled-release matrix polymer (and optional excipients) and casting/coating/extruding the resulting mass into an oral film dosage.

The enteric-release beads are generally formed by dissolving an effective amount, of opioid agonist and/or pharmaceutically acceptable salt thereof and an effective amount of opioid antagonist and/or pharmaceutically acceptable salt thereof in a non-polar (i.e. non-aqueous) solvent, particularly a solvent selected from ethanol or acetone, to form an active ingredient solution. The at least one enteric-release polymer is then admixed into the active ingredient solution while mixing to dissolve the enteric-release polymer and form an enteric-release bead solution. In advantageous embodiments, the enteric-release bead solution includes from about 1.0 to 30.0 weight % opioid agonist and/or pharmaceutically acceptable salt thereof; from about 1.0 to 20.0 weight % of opioid antagonist and/or pharmaceutically acceptable salt thereof; from about 1 to 60.0 weight % enteric-release polymer and from about 30 to 80% non-polar solvent, all based upon the weight of the enteric-release bead solution.

The enteric-release beads are harvested from the enteric-release bead solution in a two step process: nucleation and hardening. First, relatively soft enteric-release beads are formed within the enteric-release bead solution by cooling the enteric-release bead solution to below room temperature and slowly adding a polar nucleation concentrate to the enteric-release bead solution, as it is being gently mixed (i.e. the nucleation step). Upon formation of the pre-harvested soft enteric-release beads, additional polar solvent is then added slowly to the pre-harvested enteric-release bead solution as it remains under cooling and gentle mixing to harden the enteric-release beads (i.e. the hardening step). The hardened enteric-release beads are subsequently harvested from the resulting suspension via filtration or the like.

In forming the enteric-release beads, the enteric-release bead solution and/or nucleation concentrate and/or secondary polar solvent is cooled to below room temperature (i.e. about 23° C.), such as to a temperature ranging from 0 to 20° C., preferably around either 15 to 20° C. (mild temperature nucleation) or 0 to 4° C. (low temperature nucleation). The enteric-release bead solution is then subjected to relatively gentle, non-turbulent mixing, such as a mixing at a rate of less than 6,000 rpm, particularly a mixing rate of about 500 rpm to 2000 rpm. The foregoing suppressed temperature and non-turbulent mixing (i.e. mixing at speeds that not sufficiently elevated to induce homogenization) are advantageously maintained throughout both steps of the bead harvest process, i.e. during addition of the nucleation concentrate and additional polar solvent. The temperature and stir speeds may be kept constant throughout the entire bead harvest process, i.e. throughout both, the nucleation and hardening steps. Alternatively, different temperatures and/or stir speeds may be used within the nucleation and hardening steps.

The polar nucleation concentrate is generally formed by mixing a bead stabilizer in polar solvent, preferably water. The bead stabilizer is typically present within said nucleation concentrate in amounts ranging from about 0.5 to 10 weight %, such as from about 0.75 to 10 weight %, based upon the weight of the nucleation concentrate. As noted above, the nucleation concentrate is then slowly admixed into the gently stirred, cooled enteric-release bead solution dropwise until relatively soft, gelatinous enteric-release beads are formed within the pre-harvested enteric-release bead solution. An exemplary flow rate for nucleation concentrate addition generally ranges from about 1 to 2 drops/second, with each drop typically containing from about 25 to 35 microliters of concentrate. Although higher drop-rates are preferred, if the soft enteric-release beads begin to form clumps, i.e. the beads begin to fuse to one another, the nucleation concentration flow rate is reduced until such clumping stops.

The nucleation concentrate is typically added in a moderate excess in comparison to the enteric-release bead solution. The nucleation concentrate is thus typically present in at least 1:1 weight ratio, such as 1:1 to 2:1 weight ratio, particularly an about 1.3:1 weight ratio (nucleation concentrate weight:enteric-release bead solution weight) within the pre-harvested enteric-release bead solution. In that regard, sufficient nucleation concentrate is added to the enteric-release bead solution to result in bead stabilizer amounts that typically range from about 1 to 10 wt %, such as from 3 to wt %, particularly about 4 wt %, based on the weight of the resulting dried enteric-release beads, as noted above.

Upon completion of the bead stabilizer addition (i.e. completion of the nucleation concentrate addition) additional, secondary polar solvent, such as water, is then added dropwise, typically at a rate of about 5 g per minute, to the pre-harvest enteric-release bead solution to harden the beads, as the pre-harvest enteric-release bead solution remains under cooling and gentle mixing. Sufficient polar solvent is added dropwise under gentle mixing to harden the soft enteric-release beads adequately to withstand subsequent separation from the solution, e.g. via filtration or the like. The polar solvent is typically added in at least a moderate excess in comparison to the pre-harvest enteric-release bead solution containing the polar nucleation concentrate, such as at a weight ratio of about 1:1.25 to 1:4, particularly about 1:1.50 to 1:2.0 (weight of pre-harvest enteric-release bead solution containing the polar nucleation concentrate:weight of additional polar solvent). The rate of addition of polar solvent is likewise gentle, with an exemplary flow rate for secondary polar solvent addition generally ranging from about 1 to 10 grams/minute.

In hardening the soft enteric-release beads, the enteric-release bead solution is kept at a depressed temperature, such as a temperature below room temperature (i.e. about 23° C.), particularly a temperature ranging from 0 to 20° C., preferably around either 15 to 20° C. (mild temperature nucleation) or 0 to 4° C. (low temperature nucleation). The enteric-release bead solution is similarly subjected to gentle, non-turbulent, mixing, during addition of the secondary solvent, such as a mixing at a rate of less than 6000 rpm, particularly about 200 rpm to 2000 rpm, preferably from about 250 rpm to 1000 rpm. As noted above, the temperature and mixing speed during secondary solvent addition may be the same or different from the mixing speed used during the formation of the soft enteric-release beads.

The resulting hardened enteric-release beads suspended within the solvent are separated out of the solvent via filtration or the like and dried.

In the alternative, enteric-release beads suitable for use in the inventive film dosages may be formed by any other means known in the art, such as by spray-drying and the like.

Although not wishing to be bound by theory, Applicants hypothesize that the non-polar enteric-release polymer and active ingredients within the enteric-release bead solution undergo phase inversion as the polar nucleation concentrate is slowly added, resulting in the formation of a soft bead structure.

Optimal stir speeds, i.e. the minimum stir speed possible to ensure adequate mixing; cooler pre-harvest and harvest temperatures; and slower nucleation concentrate and/or polar solvent addition rates all individually promote enteric-release bead stability during both the pre-harvest and harvest steps. Accordingly, one or more of the foregoing variables may be adjusted accordingly at the onset of dumping during either the pre-harvest or harvest steps.

The controlled-release composition is generally formed by charging water into a vessel under mixing and adjusting the pH of the water to about 2 to 3 units below the opioid agonist and opioid antagonist pKa by admixing pH adjuster into the aqueous solution. Enteric-release beads are then added to the pH adjusted water and stirred until dispersed. Optional sweeteners and plasticizers may subsequently be added under continued stirring. Further optional auxiliary components, including flavor, cooling agents and surfactants may then be added to the aqueous solution, with stirring continued until the solution is uniform. The enteric-release polymer(s) may then be slowly added to the uniform solution under continuous mixing until a homogeneous coating mass, i.e. the controlled, release composition, is obtained.

Prior to film formation, the viscous homogenous coating mass can be sonicated, aspirated and/or vacuumed to remove air entrapped within the film forming composition. Alternatively, one or more antifoaming agents, e.g. insoluble oils, dimethyl polysiloxanes and other silicones, alcohol-based defoamers, stearate-based defoamers or glycol-based defoamers, can be added. The optionally deareated film forming composition is subsequently formed into a thin film having a defined wet thickness using processes well known in the art, such as by casting, coating or extrusion. More particularly, the inventive film forming composition may be cast, coated or extruded onto a suitable casting substrate, e.g. coated paper, polyethylene film or the like, thereby forming a wet film having a defined wet thickness. This wet film may then be dried, such as with a uniform laminar flow heating oven or other suitable dryers, using conventional process equipment and conditions well known to those skilled in the art, such as a drying temperature ranging from 30 to 60° C. for a drying time of 5 to 30 minutes. The dried film may then be removed from the coating substrate and subsequently be cut into various geometric shapes and sizes using a suitable cutting method, such as, die cutting, punching, knife, or rotary cutting machine.

Methods of administering the inventive oral film, dosages are also provided herein. The inventive methods of administering generally comprise either dispensing the oral film dosage to a patient for swallowing or applying the oral film dosage to the oral cavity of a patient or individual and allowing it to dissolve or disintegrate, advantageously without additional water or oral liquids other than saliva, to be subsequently absorbed in the intestinal tract of a patient or individual. Advantageously, the inventive oral film strips have a dissolution, time of less than 15 minutes, such as dissolution time of less than 5 minutes, and most preferably a dissolution time of less than 1 minute, based upon a 10 cm$^2$ oral film strip submerged in physiological fluids or an artificial simulation of such fluids.

In advantageous embodiments, the inventive methods of administration relates to the use of the inventive oral film dosages to administer a clinically effective dose of buprenorphine and naloxone to an individual for its subsequent absorption in the intestinal tract to alleviate symptoms associated with acute pain, chronic pain or suffering from addition, such as opiate addiction. Applicants respectfully submit that the advantageous binding of the active ingredients to the enteric-release polymer, particularly via pH adjustment, allows release of the active ingredient, e.g. buprenorphine and naloxone, within the intestinal tract to provide for an extended efficacy. Applicants further respectfully submit that in advantageous embodiments an individual oral film dosage provides a bioequivalent effect to a single dosage of SUBOXONE® in tablet form.

The inventive taste-masked oral film strips may be used to treat symptoms associated with any of a number of disease states or conditions, including acute or chronic pain from chronic arthritis, osteoarthritis, acute tendonitis, bursitis, headaches, migraines, chronic neuropathic pains, shingles, premenstrual symptoms, sports injuries, malignancy pain, or substance abuse syndromes, particularly opiate addiction.

The inventive oral film strips may be dispensed to an individual or patient to be self-administered as needed by the patient to alleviate symptoms associated with one or more of the foregoing disease states or conditions. Alternatively, the oral film strip may be applied, particularly by a medical professional, to the oral cavity of a patient, especially by means of mucoadhesive(s) to adhere to the mucosal membranes, such as the surfaces of the cheek, palate or tongue, for embodiments that do not include mucoadhesive(s) within the oral film dosage.

The inventive oral film strips generally take effect beginning after about 30 to 45 minutes, with the effect lasting up to 6 hours. Consequently, the inventive oral film strips are very robust, with, fast onset, low dosage amount in comparison to conventional tablets, easily transported, and easily administered with long shelf life, and further provide more extended relief in comparison to conventional oral film dosages.

While the opiate-containing enteric-release beads have been described herein within respect to disintegrating oral wafers or thin films, the inventive opiate-containing enteric-release beads may be incorporated into a wide variety of pharmacologically acceptable solid dosage forms. For example, the opiate-containing enteric-release beads may be incorporated into an orally disintegrating tablet that rapidly disintegrates in the oral cavity and releases the active ingredient to be swallowed.

In that regard, the enteric-release bead technology described in this invention can be applied to any known dosage forms, including films, tablets, oral liquids, creams, etc. Particularly, any dosage form may be formed by forming a mixture of active ingredient containing enteric-release beads, controlled release polymer(s), pH adjuster, and optional additives in the same ratios described in this invention. The resulting mixtures can be either in solid or liquid form, provided that the liquid form can be lyophilized to rid of the solvents if the dosage form is intended to be compressed into tablets.

Applicants further note that the inventive oral film dosages are useful to deliver various active pharmaceutical ingredients contained in an enteric-release bead. The inventive oral film dosages may be administered without water and edible liquids to allow for easy patient adherence and compliance especially for the young and certain general and geriatric patients who have difficulty swallowing.

WORKING EXAMPLES

The non-limiting example which follows is provided solely to illustrate particularly advantageous embodiments of the invention and expedient associated methods for forming the same.

The inventive oral film strips are formed at ambient temperatures, i.e. a temperature of approximately 23° C., and atmospheric pressure, unless indicated to the contrary or otherwise obvious from the context.

Comparative Example 1

A bead solution containing Ketoprofen was produced from a composition described in Table I:

TABLE I

| Ingredient | Quantity (g) |
| --- | --- |
| Ketoprofen | 15.07 |
| Polymethyacrylate | 5.01 |
| Ethanol | 40.01 |
| Total | 60.09 |

About 40 g ethanol was charged into a vessel as solvent. About 15 g of Ketoprofen and about 5 g of EUDRAGIT® L 100 as polymethacrylate was added to the solvent and mixed until dissolved to form a polymer phase.

Beads were then formed and harvested from the foregoing polymer phase using the ingredients in Table II:

TABLE II

| Ingredient | Quantity (g) |
| --- | --- |
| $CaCl_2$ | 0.5 |
| Surfactant | 0.13 |
| HPMC | 0.81 |
| Purified Water | 350.02 |
| Total | 351.46 |

About 0.5 g $CaCl_2$ as de-aggregating agent, about 0.13 g Polysorbate 80 as surfactant and about 0.8 g of HPMC Polymer, METOLOSE® 60HS50, was dissolved in about 350 g purified water and cooled to 4° C. to form a water phase. Under homogenization at 6,500 rpm, the water phase was added very slowly to the polymer phase. The mixture was filtered to obtain the beads. The resulting beads were found to be very soft and aggregated.

Comparative Example 2

A bead solution containing Ketoprofen was produced from a composition described in Table III:

TABLE III

| Ingredient | Quantity (g) |
| --- | --- |
| Polymethacrylate | 5.06 |
| Ketoprofen | 15.06 |
| Ethanol | 40.47 |
| Total | 70 |

About 40 g ethanol was charged into a vessel as solvent. About 15 g of Ketoprofen and about 5 g of EUDRAGIT® L 100 as polymethacrylate was then added to the solvent and mixed via overhead stirrer until dissolved to form an organic phase.

Beads were then formed and harvested from the foregoing polymer phase using the ingredients in Table IV:

TABLE IV

| Ingredient | Quantity (g) |
| --- | --- |
| HPMC Polymer | 0.5 |
| Step 1 Purified Water | 50.02 |
| Step 2 (Secondary) Purified Water | 170 |
| Total | 220.52 |

About 0.5 g of HPMC Polymer, METOLOSE®, was added to the Step 1 Purified Water and mixed until dissolved to form an aqueous phase. The aqueous phase was cooled to between 15 to 20° C. and added to the organic phase dropwise with a dropper, slowly and carefully, while the organic phase was stirred at 1000 rpm. Beads formed upon addition of the aqueous phase, but were soft. Stirring was continued for 10 minutes. About one half of the soft bead solution was removed and allowed to sit. This portion of the soft bead solution eventually coalesced. The remaining half of the soft bead solution was maintained under stirring while the secondary wafer, likewise cooled to 15 to 20° C., was added dropwise, hardening the ketoprofen/polymethacrylate beads and forming a suspension thereof. The hardened beads were removed from the suspension via filtration using a Buchner funnel and Whatman #4 filter. Spherical, hard beads were obtained, the beads were then transferred to a petri dish and vacuum dried. The resulting beads were spherical and uniform.

The beads were subjected to dissolution testing. At pH 4.5 buffer, the beads released 15 to 18% of the drug, while at pH 7.4 buffer, the beads released 98 to 100% of the drug within the first 5 minutes of testing, thereby confirming the enteric release nature of the beads.

Comparative Example 3

Comparative Example 2 was generally repeated based upon the materials described in Tables V and VI and process conditions which follow:

TABLE V

| Ingredient | Quantity (g) |
| --- | --- |
| Polymethacrylate (EUDRAGIT ® L100-55) | 5.05 |
| Ketoprofen | 15.03 |
| Acetone | 40.06 |
| Total | 60.14 |

About 40 g acetone was charged into a vessel as solvent. About 15 g of Ketoprofen was admixed into the acetone and the solution mixed to dissolve at 450 rpm. About 5 g of EUDRAGIT® L 100-55 as polymethacrylate was then added to the solvent/ketoprofen composition and mixed at 450 rpm to dissolve, thereby forming an organic phase.

Beads were then formed and harvested from the foregoing polymer phase using the ingredients in Table VI:

TABLE VI

| Ingredient | Quantity (g) |
| --- | --- |
| HPMC Polymer | 0.56 |
| Step 1 Purified Water | 50.25 |
| Step 2 (Secondary) Purified Water | 340 |
| Total | 390.25 |

About 0.56 g of HPMC Polymer, METOLOSE®, was added to the Step 1 Purified Water and mixed until dissolved to form an aqueous phase. The aqueous phase was cooled to 15 to 20° C. and then added to the organic phase dropwise with a dropper, slowly and carefully, while the organic phase was stirred. Beads formed upon addition of the aqueous phase, but were soft. Stirring was continued while the secondary water, likewise cooled to 15 to 20° C., was added dropwise, hardening the ketoprofen/polymethacrylate beads and forming a suspension thereof. The hardened beads were removed from the suspension via filtration using a Buchner funnel and Whatman #4 filter. The hardened beads were then transferred to a petri dish and vacuum dried. The resulting beads were generally spherical or rounded amorphous in shape, and far less uniform than the beads obtained in Comparative Example 2.

Example 1

Buprenorphine salt was converted to buprenorphine free base by dissolving about 1.62 grams of buprenorphine hydrochloride through the gradual addition of about 165 gm water (about a 12 step water add) to form a buprenorphine solution. About 0.13 gm NaOH was dissolved in 10 gm water, and then added dropwise to the buprenorphine solution to form a precipitate. The buprenorphine solution was centrifuged at 4,0000 rpm for about 30 minutes, and the resulting precipitated buprenorphine free base (about 1.5 gm) collected.

An enteric-release bead solution containing Buprenorphine free base was then produced from the composition described in Table VII:

TABLE VII

| Ingredient | Quantity (g) |
| --- | --- |
| Buprenorphine free base | 1.5 |
| Polymethyacrylate 1 | 1.5 |
| Acetone | 60 |
| Total | 62 |

About 1.5 g buprenorphine tree base (suspended in about 7.4 grains water) and 0.5 g Polymethacrylate 1 (as EUDRAGIT® L-100 emulsion containing 0.506 g polymer in 1.0 g water) were initially added to 4 grams of acetone under mixing in a beaker. About 15 g acetone was then added to the mixture within the beaker under continuous stirring, followed by a further addition of about 44 grams of acetone, until the polymethacrylate and buprenorphine were dissolved, thereby forming the enteric-release bead solution.

The enteric-release beads were then formed and harvested from the foregoing enteric-release bead solution using the ingredients in Table VIII:

TABLE VIII

| Ingredient | Quantity (g) |
| --- | --- |
| HPMC Polymer | 1 |
| Step 1 Purified Water | 100 |
| Step 2 (Secondary) Purified Water | 200 |
| Total | 301 |

About 1 g of HPMC Polymer, METOLOSE® 60HS50, was added to the Step 1 Purified Water and mixed until dissolved to form a nucleating polymer concentrate. The nucleating polymer concentrate was then cooled to 15 to 20° C. and then added dropwise at about 35 microliters per second to the enteric-release bead solution described in Table VII while stirring at a speed of about 350 rpm, resulting in the formation of soft beads. The Step 2 (Secondary) Purified Water, likewise cooled to 15 to 20° C., was then added dropwise at a rate of 50 g/10 minutes to the enteric-release bead solution containing the nucleating polymer concentrate (i.e. the solution containing the soft enteric-release beads), as the solution was stirred at a speed of about 500 rpm to harden the enteric-release beads. The stir speed was then reduced to 250 rpm, and the hardened enteric-release beads were subsequently harvested and examined under a microscope. The harvested enteric-release beads were generally polygonal in shape and approximately 30 microns to 100 microns in width.

Example 2

An enteric-release bead solution containing Buprenorphine and Naloxone could further be produced from the advantageous exemplary compositions described in Table IX:

TABLE IX

| Ingredient | Quantity (g) |
| --- | --- |
| Buprenorphine or other agonists | 1-12 |
| Naloxone or other agonists | 0.25-3 |
| Polymethyacrylate 1 | 0.5-1.5 |
| Polymethacrylate 2 | 0.5-1.5 |
| Ethanol or Acetone | 50-100 |
| Total | 52.25-118 |

About 50 to 100 g ethanol or acetone may be charged into a vessel as solvent. About 1 to 12 g of Buprenorphine and about 0.25 to 3 g of Naloxone will then be added to the solvent and mixed until dissolved. About 0.5 to 1.5 g of EUDRAGIT® E as Polymethacrylate 1, a film-forming polymer which will dissolve within the stomach, and about 0.5 to 1.5 g of EUDRAGIT® L or S as Polymethacrylate 2, a film-forming polymer which will dissolve in the intestines, will then be added to the active-ingredient containing solvent mixture and mixed until dissolved, thereby forming an enteric-release bead solution.

Enteric-release beads could then be formed and harvested from the foregoing enteric-release bead solution using the ingredients in Table X:

TABLE X

| Ingredient | Quantity (g) |
| --- | --- |
| HPMC Polymer | 0.9 |
| Step 1 Purified Water | 90 |
| Step 2 (Secondary) Purified Water | 300 |
| Total | 390.9 |

About 0.0 g of HPMC Polymer, METOLOSE® 60HS50, can be added to the Step 1 Purified Water and mixed until dissolved to form a nucleating polymer concentrate. The nucleating polymer concentrate will then be cooled, such as to a temperature ranging about 15 to 20° C. The nucleating polymer concentrate will then be added dropwise to the enteric-release bead solution described in Table IX as it is being maintained at a temperature of about 15 to 20° C. while stirring at a speed of about 200 to 1000 rpm. The Step 2 (Secondary) Purified Water, likewise cooled to about 15 to 20° C., can then be added dropwise to the enteric-release bead solution containing the nucleating polymer concentrate, as the solution is being held at a temperature of about 15 to 20° C. while stirring at a speed of about 100 to 1000 rpm.

The resulting suspended enteric-release beads can be harvested from the solution by filtration, for example using a Bruckner funnel or the like.

An inventive Film Dosage Coating Mass incorporating the Enteric-release Beads could then be formed from the ingredients of Table XI:

TABLE XI

| Ingredient | Quantity (g) |
| --- | --- |
| Enteric-release Beads | 30.0 |
| Controlled Release Matrix Polymers | 50.0 |
| Flavoring Agent | 4.0 |
| Surfactants | 3.0 |
| pH Adjuster | 5.0 |
| Cooling Agent | 2.0 |
| Sweeteners | 1.0 |
| Plasticizer | 5.0 |
| Total | 100 |

About 100 g of purified water can be charged into a vessel and mixed. The pH of the solution will then be adjusted to 3 units below the pKa of the buprenorphine and naloxone using one or more of citric acid, sodium citrate, tartaric acid, sodium tartrate, acetic acid, sodium acetate or the like. The enteric-release beads will be added and stirred until mixed well. Sweeteners and plasticizers will be added next and the stirring continued. The flavouring agent, cooling agents and surfactants will be pre-mixed and added to the formulation, with continued stirring until uniform. The controlled release matrix polymer will then be added slowly while mixing until a homogeneous coating mass is obtained. The coating mass will then be formed into mono-layered film using a manual coater with a suitable coating gap and a drying temperature of 30 to 60° C. for 5 to 15 minutes. The monolayer film will then be cut to suitable size, based upon the buprenorphine and naloxone doses needed for a given application.

By way of summary, the present invention thus generally concerns:

(1) An oral film dosage comprising at least one layer formed from a controlled-release composition imparting intestinal release of a therapeutically effective amount, of an opioid agonist and/or pharmaceutically acceptable salt thereof and a clinically effective amount of opioid antagonist and/or pharmaceutically acceptable salt thereof;

said controlled-release composition comprising at least one controlled-release matrix polymer and enteric-release beads dispersed within said matrix polymer, wherein said enteric-release beads are formed from an at least one enteric-release polymer having said opioid agonist and said opioid antagonist and/or their respective salts encapsulated therein;

said controlled-release composition further comprising a pH adjuster in an amount effective to adjust the composition to a pH of about 2.0 to 3.0 pH units below the pKa of the opioid agonist, antagonist and their respective salts, and said controlled-release composition further optionally comprising one or more additives selected from taste masking agents, emulsifiers, plasticizers, colorants, antioxidants, microbial preservatives and permeation enhancers, said enteric-release beads further optionally comprising bead stabilizer.

(2) An oral film dosage as in (1), wherein the enteric-release polymer is selected from one or more of hydroxypropyl methyl cellulose acetate succinate, hydroxypropyl methyl cellulose phthalate, cellulose acetate phthalate, polyvinyl acetate phthalate, and polymethylacrylate copolymer.

(3) An oral film dosage as in (2), wherein the enteric-release polymer is polymethacrylate copolymer and the polymethacrylate copolymer is a mixture of (i) cationic copolymer derived from dimethylaminoethl methacrylate and/or other neutral methacrylic acid esters and (ii) anionic copolymer derived from methacrylic acid and acrylate.

(4) An oral film dosage as in (3), wherein the cationic copolymer is a poly(butyl methacrylate, (2-dimethyl aminoethyl) methacrylate, methyl methacrylate copolymer and the anionic copolymer is derived from methacrylic acid and either methyl methacrylate or ethyl acrylate.

(5) An oral film dosage as in (4), wherein the poly(butyl methacrylate, (2-dimethyl aminoethyl) methacrylate methyl methacrylate copolymer has a ratio of respective monomers of 1:2:1 and the anionic copolymer derived from methacrylic acid and either methyl methacrylate or ethyl acrylate has a ratio of respective monomers of either 1:1 or 1:2.

(6) An oral film dosage as in (1), wherein the opioid agonist is selected from one or more of alfentanil, allylprodine, alphaprodine, amfepramone, amphetamine, amphetaminil, anileridine, apocodeine, apomorphine, asimadoline, axomadol, benzylmorphine, bezitramide, bremazocine, brifentanil, buprenorphine, butorphanol, carfentanil, clonitazene, codeine, cyclazocine, cyclorphan, cyprenorphine, cyprodime, deltorphin, desomorphine, dextromethorphan, dextromoramide, dextropropoxyphene, dezocine, diamorphine, diamorphone, diampromide, diacetylmorphine, dihydrocodeine, dihydrocodeinone, dihydroetorphine, dihydromorphine, dimenoxadol, dimephetamol, dimepheptanol, dimethylthiambutene, dioxyaphetyl butyrate, diphenoxylate, dipipanone, diprenorphine, dronabinol, Metenkephalin, Leuenkephalin, dynorphin A, dynorphin B, β-endorphin, eptazocine, endorphin, ethoheptazine, 14-ethoxymetopon, ethylketocyclazocine, ethylmethylthiambutene, ethylmorphine, etonitazene, etorphine, extromoramide, fencamfamine, fenethylline, fenproporex, fentanyl, a-methylfentanyl, beta-funaltrexamine, β-hydroxy-3-methylfentanyl, heroin, hydrocodone, hydromorphone, hydromorphodone, hydroxymethylmorphinan, hydroxypethidine, isomethadone, ketobemidone, kyotorphin, levo-α-acetylmethadol, levacetylmethadol, levallorphan, levomethadone, levomethadyl acetate, levallorphan, levorphanol, levophenacylmorphan, lofentanil, Lofexidine, loperamide, malbuphine, mazindol, mefenorex, meperidine, meprobamate, meptazinol, metazocine, methadone, metopon, methyldihydromorphine, methyldihydromorphinone, methylmorphine, methylnaltrexone, methylphenidate, methyprylon, metopon, mirfentanil, modafmil, morphiceptin, morphinan, morphine, myrophine, nabilone, nalbuphene, nalbuphine, nalmefene, nalorphine, naloxone, naloxone benzoylhydrazone, naltrexone, naltriben, naltrindole, naltrindole isothiocyanate, narceine, nalbuphine, nicomorphine, nor-binaltorphimine, norlevorphanol, normethadone, nalorphine, normorphine, norpipanone, noscapine, ohmefentanyl, o-methylnaltrexone, opium, onitazene, oxycodone, oxymorphone, papaveretum, papaverine, paregoric, pemoline, pemoline, pentazocine, pethidine, phendimetrazine, phendimetrazone, phenmetrazine, phenadoxone, phenomorphan, phenazocine, phenoperidine, pholcodeine, piminodine, pipradrol, piritramide, prenorphine, profadol, properidine, propheptazine, promedol, properidine, propiram, propoxyphene, propylhexedrine, remifentanil, spiradoline, sufentanil, sufentanyl, tapentadol, thebaine, tramadol, trefentanil, tilidine, viminol or their salts, or opioids of the phenanthrene, morphinan, benzomorphan, methadone, phenylpiperidine, propionanilide 4-anilidopiperidine, 4-aryl piperidines, and 4-heteroarylpiperidines class.

(7) An oral film dosage as in (1), wherein the opioid agonist is buprenorphine and/or a pharmaceutically acceptable salt thereof.

(8) An oral film dosage as in (1), wherein the opioid antagonist is selected from one or more of alazocine, amiphenazole, butorphanol, chlornaltrexamine, clocinnamox, cyclazacine, cyclazocine, cyclorphan, cyprenorphine, diprenorphine, etazocine, β-funaltrexamine, levallorphan, meptazinol, metazocine, nadide, nalbuphine, nalide, nalmefene, nalmefendiprenorphine, nalmexone, nalorphine, nalorphine dinicotinate, naloxone, 6-amino-naloxone, N-methylnaloxone, nor-binaltorphimine, naltrendol, naltrexone, 6-amino-naltrexone, 7-benzylidenenaltrexone, N-methylnaltrexone, naltrindole, naluphine, oxilorphan, pentazocine, piperidine-N-alkylcarboxylate opioid antagonists, and opioid antagonist polypeptides.

(9) An oral film dosage as in (1), wherein the opioid antagonist is naloxone and/or a pharmaceutically acceptable salt thereof.

(10) An oral film dosage as in (1), wherein said controlled-release matrix polymer is a film forming polymer selected from one or more of cellulose and/or derivatives thereof; synthetic or natural gum, acrylic polymer and/or copolymer thereof, polyalkylene oxide, polyalkylene glycol, pullulan, polyvinyl pyrrolidone, polyvinyl alcohol, carrageanan, alginic acid and/or salts thereof, carboxyvinyl polymers, pectin and/or derivatives thereof, xanthan gum and/or derivatives thereof and starch and/or derivatives thereof.

(11) An oral film dosage as in (10), wherein said cellulose and/or derivative thereof is methyl cellulose, ethyl cellulose, hydroxyethyl cellulose, hydroxypropyl cellulose, hydroxypropylmethyl cellulose, carboxymethyl cellulose, sodium carboxymethyl cellulose or a mixture thereof; said synthetic or natural gum is xanthan gum, tragacanth gum, guar gum, acacia gum, arabic gum, locust bean gum or mixtures thereof, said acrylic polymer and/or copolymer thereof is methacrylic acid polymer, methacrylic acid copolymer, acrylic acid polymers, acrylic acid copolymers, polyacrylamide or mixture thereof and said starch is bean starch, pea starch or mixtures thereof.

(12) An oral film dosage as in (1), wherein said controlled-release matrix polymer is a mucoadhesive polymer selected from one or more of edible silicone, polyacrylic acids, and polymers of acrylic acid cross-linked with polyalkenyl ethers or divinyl glycol.

(13) An oral film dosage as in (1), wherein said controlled-release matrix polymer comprises a combination of two or more water, acetone and alcohol soluble polymers.

(14) An oral film dosage as in (1), wherein said and said oral film dosage further comprises one or more taste masking ingredients, and said taste masking ingredients are selected from one or more of sweeteners, cooling sensation agents, taste receptor blockers, and flavors.

(15) An oral film dosage as in (14), wherein said sweetener is one or more of dextrose, lactose, fructose, mannitol, sucrose, trehalose, sucralose, xylitol, mannitol aspartame, saccharin, sorbitol, sodium saccharin, sodium cyclamate, acesulfame, honey, isomalt, maltodextrin, dextrin and dextrate, said cooling sensation agent is menthol, said taste receptor blocker is one or more of polyethoxylated castor oil or ion exchange resin, and said flavor is one or more of essential oils or extracts of menthol, wintergreen, peppermint, sweet mint, spearmint, vanillin, cherry, butterscotch, chocolate, cinnamon, clove, lemon, orange, raspberry, rose, spice, violet, herbal, fruit, strawberry, grape, pineapple, vanilla, peppermint, peach, kiwi, papaya, mango, coconut, apple, coffee, plum, watermelon, nuts, green tea, grapefruit, banana, butter, or chamomile.

(16) An oral film dosage as in (1), wherein said film dosage further comprises one or more emulsifiers.

(17) An oral film dosage as in (16), wherein said emulsifier is selected from one or more of castor oil derivatives, cetyl and palmityl alcohol, ethanol, hydrogenated vegetable oils, polyvinyl alcohol, simethicone, sorbitan ester, glyceryl monostearate, polyoxyethylene alkyl ethers, polyoxyethylene stearates, poloxamer, and polyoxyethylene sorbitan fatty acid esters.

(18) An oral film dosage as in (1), wherein said film dosage further comprises one or more plasticizers selected from alkylene glycols, polyalkylene glycols, glycerol, triacetin, deacetylated monoglyceride, polyethylene glycols, diethyl salate, and triethyl citrate.

(19) An oral film dosage as in (1), wherein said film dosage further comprises one or more colorants selected from edible pigments, dyes, natural food colors and synthetic colorants.

(20) An oral film dosage as in (1), wherein said film dosage further comprises one or more antioxidants selected from chelating agents, sodium bisulfite, sodium metabisulfite, ascorbic acid, and ascorbyl palmitate.

(21) An oral film dosage as in (20), wherein said chelating agents are one or more of ethylenediaminetetraacetic acid or ethylene glycol tetraacetic acid (22) An oral film dosage as in (1), wherein said film dosage further comprises one or more microbial preservatives selected from butylated hydroxyanisol, butylated hydroxyltoluene, parabens and derivatives thereof, sorbic acids and derivatives thereof, benzoic acid and derivatives thereof, propionic acid and derivatives thereof and acetic acid and derivatives thereof.

(23) An oral film dosage as in (1), wherein said film dosage further comprises a permeation enhancer selected from one or more of anionic surfactants, cationic surfactants, non-ionic surfactants, bile salts, sodium glycodeoxycholate, sodium glycocholate, sodium taurodeoxycholate, sodium taurocholate, fatty acids, cyclodextrins, chelators, sodium citrate, polyacrylates, polysaccharide polymers and cationic amino acids.

(24) An oral film dosage as in (23), wherein said anionic surfactants are sodium lauryl sulfate and/or sodium laurate, said cationic surfactant is cetylpyridium chloride said nonionic surfactants is poloxamer, polyoxyethylene surfactant, sorbitan monolaurate, polyethylene glycol-100 stearate and/or Polysorbate 20, said fatty acid is oleic and/or caprylic acid; said cyclodextrin is α-, β-, γ-cyclodextrin, and/or methylated β-cylcodextrins; said chelator is ethylenediaminetetraacetic acid and/or ethylene glycol tetraacetic acid; said polysaccharide polymer is chitosan and/or trimethyl chitosan and said cationic amino acids are poly-L-arginine and/or L-lysine.

(25) An oral film dosage as in (1) wherein said clinically effective amount of said opioid agonist within said film is greater than 2 milligrams for opioid addiction treatment dosages; about 100 to 400 micrograms for acute pain treatment dosages and from about 20 to 70 micrograms per hour for chronic pain dosages; and said clinically effective amount of opioid antagonist is a subtherapeutic amount, ranging from greater than 0.5 milligrams for opioid addiction treatment dosages; about 25 to 100 micrograms for acute pain treatment dosages and from about 5 to 17.5 micrograms per hour for chronic pain treatment dosages.

(26) An oral film dosage as in (1), wherein said controlled-release layer includes controlled-release matrix polymer in an amount ranging from about 30.0 to 70.0 weight % and enteric-release beads ranging in amount from about 5.0 to 50 weight % dispersed within said matrix polymer, and the effective amount of the pH adjuster ranges from about 3.0 to 10.0 weight %, all based on the weight of the controlled-release layer.

(27) An oral trim dosage as in (1), wherein said film dosage is a single-layered film.

(28) An oral film dosage as in (1), wherein said film dosage is a multi-layered film further comprising a mucoadhesive layer.

(29) An oral film dosage as in (1), where the dosage has a round, oval, square, rectangular or other irregular geometric shape.

(30) A method of making an oral film dosage as in (1), said method comprising
(a) forming enteric-release release beads by
  (i) dissolving an effective amount of opioid agonist and/or pharmaceutically acceptable salt thereof and an effective amount of opioid antagonist and/or pharmaceutically acceptable salt thereof in a non-aqueous solvent selected from ethanol or acetone to form an active ingredient solution;
  (ii) admixing at least one enteric-release polymer into the active ingredient solution and mixing to dissolve said enteric-release polymer to form an enteric-release bead solution
  (iii) admixing a bead stabilizer in a polar solvent to form a nucleation concentrate;
  (iv) admixing the nucleation concentrate dropwise into the enteric-release bead solution to form pre-harvested enteric-release beads;
  (v) hardening the pre-harvested enteric-release beads by admixing secondary polar solvent into the enteric-release bead solution containing the nucleation concentrate; and
  (vi) harvesting the hardened enteric-release beads from the enteric-release bead solution via filtration;
(b) forming the controlled-release composition by
  (i) adjusting the pH of an aqueous solution to 3 units below the opioid agonist and opioid antagonist pKa;
  (ii) adding the harvested enteric-release beads;
  (iii) adding optional processing and/or flavor masking constituents;
  (iv) adding at least one controlled-release matrix polymer to form the controlled-release coating composition;
(c) forming the oral film dosage by
  (i) coating at least one layer of the controlled-release coating composition
  (ii) drying the coated controlled-release coating to form a controlled-release layer;
  (iii) cutting the dried controlled-release into a geometric shape containing an effective amount of opioid agonist and/or salt thereof and an effective amount of opioid antagonist and/or salt thereof.

(31) A method of making an oral film dosage as in (30), said method further comprising forming a premix comprising said optional processing and/or flavor masking constituents.

(32) A method of making an oral film dosage as in (30), wherein said polar solvent and secondary polar solvent is water.

(33) A method of treatment for chronic arthritis, osteoarthritis, acute tendonitis, bursitis, headaches, migraines, chronic neuropathic pains, shingles, premenstrual symptoms, sports injuries, malignancy pain or substance abuse syndromes comprising administering an oral film dosage as in 1 by dispensing the film dosage to a patient or placing the film dosage in the mouth cavity of a patient with subsequent release of a therapeutically effective dose of opioid agonist and a clinically effective dose of opioid antagonist in the intestinal tract.

(34) A method of treatment as in (33), wherein said oral film dosage is administered in the absence of water or liquids other than saliva.

It is understood that various other modifications will be apparent to and can be readily made by those skilled in the art without departing from the scope and spirit of this invention. Accordingly, it is not intended that the scope of the claims appended hereto be limited to the description as set forth herein, but rather that the claims be construed as encompassing all the features of patentable novelty that reside in the present invention, including all features that would be treated as equivalents thereof by those skilled in the art to which this invention pertains. Therefore, the present invention should not be limited to any single illustrative embodiment described herein. As used herein and the appended claims, the articles "a", "an" and "the" can connote either a single or plural article.

The invention claimed is:

1. An oral film dosage comprising at least one layer formed from a controlled-release composition imparting intestinal release of a therapeutically effective amount of an opioid agonist and/or pharmaceutically acceptable salt thereof and a clinically effective amount of opioid antagonist and/or pharmaceutically acceptable salt thereof;

said controlled-release composition comprising at least one controlled-release matrix polymer and enteric-release beads dispersed within said matrix polymer, wherein said enteric-release beads are formed from an at least one enteric-release polymer having said opioid agonist and said opioid antagonist and/or their respective salts encapsulated therein in the form of cores or islands, wherein the enteric-release polymer dissolves to release at least 75 wt. % of said opioid agonist and said opioid antagonist and/or their respective salts in an aqueous solution at a pH of 7.4, said enteric-release polymer is polymethacrylate copolymer and the polymethacrylate copolymer is a mixture of (i) cationic copolymer derived from dimethylaminoethl methacylate and/or other neutral methacrylic acid esters and (ii) anionic copolymer derived from methacrylic acid and acrylate, wherein the weight ratio of said cationic copolymer and said anionic copolymer is about 1:5 to 5:1;

said controlled-release composition further comprising a pH adjuster in an amount effective to adjust the composition to a pH of about 2.0 to 3.0 pH units below the pKa of the opioid agonist, antagonist and their respective salts, and said controlled-release composition further optionally comprising one or more additives selected from taste masking agents, emulsifiers, plasticizers, colorants, antioxidants, microbial preservatives and permeation enhancers, said enteric-release beads further optionally comprising bead stabilizer;

said cores or islands consisting essentially of said opioid agonist and/or said opioid antagonist or their respective salts.

2. An oral film dosage as claimed in claim 1, wherein the enteric-release polymer is polymethacrylate copolymer and the polymethacrylate copolymer is a mixture of (i) cationic copolymer derived from dimethylaminoethl methacylate and/or other neutral methacrylic acid esters and (ii) anionic copolymer derived from methacrylic acid and acrylate and the entirety of the active ingredient passes through the stomach for release within the intestines.

3. An oral film dosage as claimed in claim 2, wherein the cationic copolymer is a poly (butyl methacrylate), (2-dimethyl aminoethyl) methacrylate, methyl methacrylate copolymer and the anionic copolymer is derived from methacrylic acid and either methyl methacrylate or ethyl acrylate.

4. An oral film dosage as claimed claim 3, wherein the poly (butyl methacrylate, (2-dimethyl aminoethyl) methacrylate methyl methacrylate copolymer has a ratio of respective monomers of 1:2:1 and the anionic copolymer derived from methacrylic acid and either methyl methacrylate or ethyl acrylate has a ratio of respective monomers of either 1:1 or 1:2.

5. An oral film dosage as claimed in claim 1, wherein the opioid agonist is selected from one or more of alfentanil, allylprodine, alphaprodine, amfepramone, amphetamine, amphetaminil, anileridine, apocodeine, apomorphine, asimadoline, axomadol, benzylmorphine, bezitramide, bremazocine, brifentanil, buprenorphine, butorphanol, carfentanil, clonitazene, codeine, cyclazocine, cyclorphan, cyprenorphine, cyprodime, deltorphin, desomorphine, dextromethorphan, dextromoramide, dextropropoxyphene, dezocine, diamorphine, diamorphone, diampromide, diacetylmorphine, dihydrocodeine, dihydrocodeinone, dihydroetorphine, dihydromorphine, dimenoxadol, dimephetamol, dimepheptanol, dimethylthiambutene, dioxyaphetyl butyrate, diphenoxylate, dipipanone, diprenorphine, dronabinol, Metenkephalin, Leuenkephalin, dynorphin A, dynorphin B, β-endorphin, eptazocine, eridorphin, ethoheptazine, 14-ethoxymetopon, ethylketocyclazocine, ethylmethylthiambutene, ethylmorphine, etonitazene, etorphine, extromoramide, fencamfamine, fenethylline, fenproporex, fentanyl, a-methylfentanyl, beta-funaltrexamine, β-hydroxy-3-methylfentanyl, heroin, hydrocodone, hydromorphone, hydromorphodone, hydroxymethylmorphinan, hydroxypethidine, isomethadone, ketobemidone, kyotorphin, levo-α-acetylmethadol, levacetylmethadol, levallorphan, levomethadone, levomethadyl acetate, levallorphan, levorphanol, levophenacylmorphan, lofentanil, Lofexidine, loperamide, malbuphine, mazindol, mefenorex, meperidine, meprobamate, meptazinol, metazocine, methadone, metopon, methyldihydromorphine, methyldihydromorphinone, methylmorphine, methylnaltrexone, methylphenidate, methyprylon, metopon, mirfentanil, modafmil, morphiceptin, morphinan, morphine, myrophine, nabilone, nalbuphene, nalbuphine, nalmefene, nalorphine, naloxone, naloxone benzoylhydrazone, naltrexone, naltriben, naltrindole, naltrindole isothiocyanate, narceine, natbuphine, nicomorphine, nor-binaltorphimine, norlevorphanol, normethadone, nalorphine, normorphine, norpipanone, noscapine, ohmefentanyl, o-methylnaltrexone, opium, onitazene, oxycodone, oxymorphone, papaveretum, papaverine, paregoric, pemoline, pernoline, pentazocine, pethidine, phendimetrazine, phendimetrazone, phenmetrazine, phenadoxone, phenomorphan, phenazocine, phenoperidine, pholcodeine, piminodine, pipradrol, piritramide, prenorphine, profadol, properidine, propheptazine, promedol, properidine, propiram, propoxyphene, propylhexedrine, remifentanil, spiradoline, sufentanil, sufentanyl, tapentadol, thebaine, tramadol, trefentanil, tilidine, viminol or their salts, or opioids of the phenanthrene, morphinan, benzomorphan, methadone, phenylpiperidine, propionanilide 4-anilidopiperidine, 4-aryl piperidines, and 4-heteroarylpiperidines class.

6. An oral film dosage as claimed in claim 1, wherein the opioid agonist is buprenorphine and/or a pharmaceutically acceptable salt thereof.

7. An oral film dosage as claimed in claim 1, wherein the opioid antagonist is selected from one or more of alazocine, amiphenazole, butorphanol, chlornaltrexamine, clocinnamox, cyclazacine, cyclazocine, cyclorphan, cyprenorphine, diprenorphine, etazocine, β-funaltrexamine, levallorphan, meptazinol, metazocine, nadide, nalbuphine, nalide, nalmefene, nalmefendiprenorphine, nalmexone, nalorphine, nalorphine dinicotinate, naloxone, 6-amino-naloxone, N-methylnaloxone, nor-binaltorphimine, naltrendol, naltrexone, 6-amino-naltrexone, 7-benzylidenenaltrexone, N-methylnaltrexone, naltrindole, naluphine, oxilorphan, pentazocine, piperidine-N-alkylcarboxylate opioid antagonists, and opioid antagonist polypeptides.

8. An oral film dosage as claimed in claim 1, wherein the opioid antagonist is naloxone and/or a pharmaceutically acceptable salt thereof.

9. An oral film dosage as claimed in claim 1, wherein said controlled-release matrix polymer is a film forming polymer selected from one or more of cellulose and/or derivatives thereof, synthetic or natural gum, acrylic polymer and/or copolymer thereof, polyalkylene oxide, polyalkylene glycol, pullulan, polyvinyl pyrrolidone, polyvinyl alcohol, carrageanan, alginic acid and/or salts thereof, carboxyvinyl polymers, pectin and/or derivatives thereof, xanthan gum and/or derivatives thereof, and starch and/or derivatives thereof.

10. An oral film dosage as claimed in claim 9, wherein said cellulose and/or derivative thereof is methyl cellulose, ethyl cellulose, hydroxyethyl cellulose, hydroxypropyl cellulose, hydroxypropylmethyl cellulose, carboxymethyl cellulose, sodium carboxymethyl cellulose or a mixture thereof; said synthetic or natural gum is xanthan gum, tragacanth gum, guar gum, acacia gum, arabic gum, locust bean gum or mixtures thereof, said acrylic polymer and/or copolymer thereof is methacrylic acid polymer; methacrylic acid copolymer, acrylic acid polymers, acrylic acid copolymers, polyacrylamide or mixture thereof, and said starch is bean starch, pea starch or mixtures thereof.

11. An oral film dosage as claimed in claim 1, wherein said controlled-release matrix polymer is a mucoadhesive polymer selected from one or more of edible silicone, polyacrylic acids, and polymers of acrylic acid cross-linked with polyalkenyl ethers or divinyl glycol.

12. An oral film dosage as claimed in claim 1, wherein said controlled-release matrix polymer comprises a combination of two or more water, acetone and alcohol soluble polymers.

13. An oral film dosage as claimed in claim 1, wherein said oral film dosage further comprises one or more taste masking ingredients, and said taste masking ingredients are selected from one or more of sweeteners, cooling sensation agents, taste receptor blockers, and flavors.

14. An oral film dosage as claimed in claim 13, wherein said sweetener is one or more of dextrose, lactose, fructose, mannitol, sucrose, trehalose, sucralose, xylitol, mannitol, aspartame, saccharin, sorbitol, sodium saccharin, sodium cyclamate, acesulfame, honey, isomalt, maltodextrin, dextrin and dextrate, said cooling sensation agent is menthol, said taste receptor blocker is one or more of polyethoxylated castor oil or ion exchange resin, and said flavor is one or more of essential oils or extracts of menthol, wintergreen, peppermint, sweet mint, spearmint, vanillin, cherry, butterscotch, chocolate, cinnamon, clove, lemon, orange, raspberry, rose, spice, violet, herbal, fruit, strawberry, grape, pineapple, vanilla, peppermint, peach, kiwi, papaya, mango, coconut, apple, coffee, plum, watermelon, nuts, green tea, grapefruit, banana, butter, or chamomile.

15. An oral film dosage as claimed in claim 1, wherein said film dosage further comprises one or more emulsifiers.

16. An oral film dosage as claimed in claim 15, wherein said emulsifier is selected from one or more of castor oil derivatives, cetyl and palmityl alcohol, ethanol, hydrogenated vegetable oils, polyvinyl alcohol, simethicone, sorbitan ester, glyceryl monostearate, polyoxyethylene alkyl ethers, polyoxyethylene stearates, poloxamer, and polyoxyethylene sorbitan fatty acid esters.

17. An oral film dosage as claimed in claim 1, wherein said film dosage further comprises one or more plasticizers selected from alkylene glycols, polyalkylene glycols, glycerol, triacetin, deacetylated monoglyceride, polyethylene glycols, diethyl salate, and triethyl citrate.

18. An oral film dosage as claimed in claim 1, wherein said film dosage further comprises one or more colorants selected from edible pigments, dyes, natural food colors and synthetic colorants.

19. An oral film dosage as claimed in claim 1, wherein said film dosage further comprises one or more antioxidants selected from chelating agents, sodium bisulfite, sodium metabisulfite, ascorbic acid, and ascorbyl palmitate.

20. An oral film dosage as claimed in claim 19, wherein said chelating agents are one or more of ethylenediaminetetraacetic acid or ethylene glycol tetraacetic acid.

21. An oral film dosage as claimed in claim 1, wherein said film dosage further comprises one or more microbial preservatives selected from butylated hydroxyanisol, butylated hydroxyltoluene, parabens and derivatives thereof, sorbic acids and derivatives thereof, benzoic acid and derivatives thereof, propionic acid and derivatives thereof, and acetic acid and derivatives thereof.

22. An oral film dosage as claimed in claim 1, wherein said film dosage further comprises a permeation enhancer selected from one or more of anionic surfactants, cationic surfactants, non-ionic surfactants, bile salts, sodium glycodeoxycholate, sodium glycocholate, sodium taurodeoxycholate, sodium taurocholate, fatty acids, cyclodextrins, chelators, sodium citrate, polyacrylates, polysaccharide polymers and cationic amino acids.

23. An oral film dosage as claimed in claim 22, wherein said anionic surfactants are sodium lauryl sulfate and/or sodium laurate, said cationic surfactant is cetylpyridinium chloride, said non-ionic surfactants is poloxamer, polyoxyethylene surfactant, sorbitan monolaurate, polyethylene glycol-100 stearate and/or Polysorbate 20, said fatty acid is oleic and/or caprylic acid; said cyclodextrin is α-, β-, γ-cyclodextrin, and/or methylated β-cylcodextrins; said chelator is ethylenediaminetetraacetic acid and/or ethylene glycol tetraacetic acid; said polysaccharide polymer is chitosan and/or trimethyl chitosan and said cationic amino acids are poly-L-arginine and/or L-lysine.

24. An oral film dosage as claimed in claim 1, wherein said therapeutically effective amount of said opioid agonist within said film is greater than 2 milligrams for opioid addiction treatment dosages; about 100 to 400 micrograms for acute pain treatment dosages and from about 20 to 70 micrograms per hour for chronic pain dosages; and said clinically effective amount of opioid antagonist is a subtherapeutic amount ranging from greater than 0.5 milligrams for opioid addiction treatment dosages; about 25 to 100 micrograms for acute pain treatment dosages and from about 5 to 17.5 micrograms per hour for chronic pain treatment dosages.

25. An oral film dosage as claimed in claim 1, wherein said controlled-release layer includes controlled-release matrix polymer in an amount ranging from about 30.0 to 70.0 weight % and enteric-release beads ranging in amount from about 5.0 to 50 weight % dispersed within said matrix polymer, and the effective amount of the pH adjuster ranges from about 3.0 to 10.0 weight %, all based on the weight of the controlled-release layer.

26. An oral film dosage as claimed in claim 1, wherein said film dosage is a single-layered film.

27. An oral film dosage as claimed in claim 1, wherein said film dosage is a multi-layered film further comprising a muco-adhesive layer.

28. An oral film dosage as claimed in claim 1, where the dosage has a round, oval, square, rectangular or other irregular geometric shape.

29. A method of making an oral film dosage as claimed in claim 1, said method comprising
(a) forming enteric-release release beads by
(i) dissolving an effective amount of opioid agonist and/or pharmaceutically acceptable salt thereof and an effective amount of opioid antagonist and/or pharmaceutically acceptable salt thereof in a non-aqueous solvent selected from ethanol or acetone to form an active ingredient solution;
(ii) admixing the enteric-release polymer mixture into the active ingredient solution and mixing to dissolve said enteric-release polymer mixture to form an enteric-release bead solution;
(iii) admixing a bead stabilizer in a polar solvent to form a nucleation concentrate;
(iv) admixing the nucleation concentrate dropwise into the enteric-release bead solution to form pre-harvested enteric-release beads;
(v) hardening the pre-harvested enteric-release beads by admixing secondary polar solvent into the enteric-release bead solution containing the nucleation concentrate; and
(vi) harvesting the hardened enteric-release beads from the enteric-release bead solution via filtration;
(b) forming the controlled-release composition by
(i) adjusting the pH of an aqueous solution to 3 units below the opioid agonist and opioid antagonist pKa;

(ii) adding the harvested enteric-release beads;
(iii) adding the one or more optional additives;
(iv) adding at least one controlled-release matrix polymer to form the controlled-release coating composition;
(c) forming the oral film dosage by
(i) coating at least one layer of the controlled-release coating composition
(ii) drying the coated controlled-release coating to form a controlled-release layer;
(iii) cutting the dried controlled-release into a geometric shape containing an therapeutically effective amount of opioid agonist and/or salt thereof and an clinically effective amount of opioid antagonist and/or salt thereof.

30. A method of making an oral film dosage as claimed in claim 29, said method further comprising forming a premix comprising said one or more optional additives.

31. A method of making an oral film dosage as claimed in claim 29, wherein said polar solvent and secondary polar solvent is water.

32. A multi-layered oral film dosage comprising at least one layer formed from a controlled-release composition imparting intestinal release of a therapeutically effective amount of an opioid agonist and/or pharmaceutically acceptable salt thereof and a clinically effective amount of opioid antagonist and/or pharmaceutically acceptable salt thereof;

said controlled-release composition comprising at least one controlled-release matrix polymer and enteric-release beads dispersed within said matrix polymer, wherein said enteric-release beads are formed from an at least one enteric-release polymer having said opioid agonist and said opioid antagonist and/or their respective salts encapsulated therein;

said controlled-release composition further comprising a pH adjuster in an amount effective to adjust the composition to a pH of about 2.0 to 3.0 pH units below the pKa of the opioid agonist, antagonist and their respective salts, and said controlled-release composition further optionally comprising one or more additives selected from taste masking agents, emulsifiers, plasticizers, colorants, antioxidants, microbial preservatives and permeation enhancers, said enteric-release beads further optionally comprising bead stabilizer, wherein the opioid agonist is buprenorphine and/or a pharmaceutically acceptable salt thereof, the opioid antagonist is naloxone and/or a pharmaceutically acceptable salt thereof and the pH adjuster is present in an amount effective to adjust the composition to a pH of about 4.94 to 6.31.

* * * * *

UNITED STATES PATENT AND TRADEMARK OFFICE
CERTIFICATE OF CORRECTION

| | | |
|---|---|---|
| PATENT NO. | : 9,763,879 B2 | Page 1 of 1 |
| APPLICATION NO. | : 14/390322 | |
| DATED | : September 19, 2017 | |
| INVENTOR(S) | : Michael Li | |

It is certified that error appears in the above-identified patent and that said Letters Patent is hereby corrected as shown below:

In the Specification

Column 5, Line 42, delete "a-methylfentanyl" insert --α-methylfentanyl--

Column 6, Line 63, delete "agonist" insert --antagonist--

Column 18, Line 5, delete "addition" insert --addiction--

Column 28, Line 10, delete "controlled-release" insert --controlled-release layer--

Signed and Sealed this
Seventh Day of November, 2017

Joseph Matal
*Performing the Functions and Duties of the
Under Secretary of Commerce for Intellectual Property and
Director of the United States Patent and Trademark Office*